US00RE39436E

(19) United States
(12) Reissued Patent
Spindler et al.

(10) Patent Number: US RE39,436 E
(45) Date of Reissued Patent: Dec. 19, 2006

(54) INTERVENTIONS TO MIMIC THE EFFECTS OF CALORIE RESTRICTION

(75) Inventors: Stephen R. Spindler, Riverside, CA (US); Joseph M. Dhahbi, Alameda, CA (US)

(73) Assignee: The Regents of the University of California, Oakland, CA (US)

(21) Appl. No.: 10/807,554

(22) Filed: Mar. 22, 2004

Related U.S. Patent Documents

Reissue of:
(64) Patent No.: 6,406,853
Issued: Jun. 18, 2002
Appl. No.: 09/648,642
Filed: Aug. 25, 2000

U.S. Applications:
(

(63) Continuation-in-part of application No. 09/471,224, filed on Dec. 23, 1999, now abandoned.

(51) Int. Cl.
*C12Q 1/68* (2006.01)

(52) U.S. Cl. ..... 435/6; 119/15; 119/18; 119/34; 435/5; 435/91.1; 435/91.2; 514/693; 514/724

(58) Field of Classification Search ..... 435/5, 435/6, 91.1, 91.2; 514/693, 724; 119/15, 119/18, 54
See application file for complete search history.

(56) References Cited

U.S. PATENT DOCUMENTS 6,569,624 B1 * 5/2003 Weindruch et al. ..... 435/6

FOREIGN PATENT DOCUMENTS

WO WO 01-12851 * 2/2001

OTHER PUBLICATIONS

Walford et al., "Dietary restriction and aging: historical phases, mechanisms and current directions," Journal of Nutrition vol. 117, No. 10, pp. 1650–1654 (1987).*

Goyns et al., "Differential display analysis of gene expression indicates that age–related changes are restricted to a small cohort of genes," Mechanisms of Ageing and Development vol. 101, No. 1, 2, pp. 73–90 (1998).*

Lane et al., "2–Deoxy–D–glucose feeding in rats mimics physiologic effects of calorie restriction," Journal of Anti–Aging Medicine vol. 1, No. 4, pp. 327–337 (1998).*

Weindruch et al., "Caloric Restriction Mimetics: Metabolic Interventions," J. Gerontology: Series A, vol. 56A (Special Issue 1, pp. 20–33 (2001).*

Lee et al. Science, vol. 285, Aug. 1999, pp. 1390–1393.*

Lee et al., Gene Expression Profile of Aging and Its Retardation by Caloric □□Restriction, (1999) Science 285:1390.*

Weindruch et al., Dietary Restriction in Mice Beginning at 1 Year of Age: □□Effect on Life–Span and Spontaneous Cancer Incidence, (1982) Science 215–1415.*

Chu, K., et al., "Short–term caloric restriction augments age–related decreases in gastrin content and release," *Mechanisms of Ageing and Development,* 1996, vol. 87, pp. 25–33.

Mote, P., et al., "Influence of age and caloric restriction on expression of hepatic genes for xenobiotic and oxygen metabolizing enzymes in the mouse," *Journal of Geronology: Biological Sciences,* 1991, vol. 46, No. 3, pp. B95–B100.

Tillman, J., et al., "Dietary calorie restriction in mice induces carbamyl phosphate synthetase I gene transcription tissue specifically," *The Journal of Biological Chemistry,* 1996, vol. 271, No. 7, pp. 3500–3506.

* cited by examiner

*Primary Examiner*—Robert A. Wax
(74) *Attorney, Agent, or Firm*—Townsend and Townsend and Crew LLP

(57) ABSTRACT

Long term calorie restriction has the benefit of increasing life span. Methods to screen interventions that mimic the effects of calorie restriction are disclosed. Extensive analysis of genes for which expression is statistically different between control and calorie restricted animals has demonstrated that specific genes are preferentially expressed during calorie restriction. Screening for interventions which produce the same expression profile will provide interventions that increase life span. In a further aspect, it has been discovered that test animals on a calorie restricted diet for a relatively short time have a similar gene expression profile to test animals which have been on a long term calorie restricted diet.

16 Claims, 13 Drawing Sheets

(3 of 13 Drawing Sheet(s) Filed in Color)

Effect of LT- and ST-CR on Age-related Changes in Gene Expression

Average of Pairwise Comparison of the Global Gene Expression Correlation Coefficient for Each Possible Pair of Mice

| | Young CR | Young Control | STZ-Diabetic |
|---|---|---|---|
| Young CR | 0.64 ± 0.01 | -0.07 ± 0.02 | -0.16 ± 0.01 |
| Young Control | | 0.15 ± 0.02 | 0.03 ± 0.02 |
| STZ-Diabetic | | | 0.38 ± 0.05 |

*All values calculated for average are Log (1+mRNA level)

Fig. 10

Average of Pairwise Comparison of the Global Gene Expression Correlation Coefficient for Each Possible Pair of Mice

| | Old CR | Old Control | AG-Treated |
|---|---|---|---|
| Old CR | 0.72 ± 0.01 | -0.09 ± 0.02 | -0.17 ± 0.02 |
| Old Control | | 0.21 ± 0.07 | 0.05 ± 0.01 |
| AG-Treated | | | 0.48 ± 0.02 |

Fig. 12

*All values calculated for average are Log (1+mRNA level)

INTERVENTIONS TO MIMIC THE EFFECTS OF CALORIE RESTRICTION

Matter enclosed in heavy brackets [ ] appears in the original patent but forms no part of this reissue specification; matter printed in italics indicates the additions made by reissue.

This application is a continuation in part of U.S. application Ser. No. 09/471,224, filed Dec. 23, 1999.

BACKGROUND OF THE INVENTION

1. Field of the Invention

For years, researchers have attempted to identify biomarkers of aging to facilitate the identification of interventions that might slow or reverse the aging process. Dietary calorie restriction (CR) is the only well-documented method for extending life span in homeothermic vertebrates, and is the most effective means known for reducing cancer incidence. Although many of the physiological consequences of CR were described 65 years ago, there is no consensus regarding its mode of action. Consequently, there has been no practical method of identifying interventions that might mimic such calorie-restriction effects. Rather, a researcher would have to wait the test animal's lifetime to determine whether a particular intervention impacted life-span and/or cancer incidence.

2. Description of the Related Art

Mammals seem to share a common set of genes, and yet they have widely differing life spans. It is impossible to know at present whether the differences in life spans are due to differences in the sequence of specific genes, or to differences in their expression. However, it is clear from many years of study in dozens of laboratories that long term reduction in dietary calorie consumption (CR) delays most age-related physiological changes, and extends life span in all species tested, provided malnutrition is avoided (Weindruch, et al. The Retardation of Aging and Disease by Dietary Restriction (Charles C. Thomas, Springfield, Ill., 1988)). These studies also have shown that CR is the most effective means now known for reducing cancer incidence and increasing the mean age of onset of age-related diseases and tumors in homeothermic vertebrates (Weindruch et al. (1982) Science 215: 1415). Thus, it seems clear that life spans can be extended through a relatively simple dietary regimen. However, there are no studies on the effects of short term calorie restriction on metabolism and gene expression.

One report has been published of gene expression profiling in muscle (Lee et al. (1999) Science 285: 1390) In these studies, many age related changes in muscle gene expression appeared to be prevented or reversed by CR. The expression profiles of 6500 genes were compared among old, long-term CR and control mice, and young control mice. Some age-related changes in muscle gene expression appeared to be wholly or partially prevented by CR.

SUMMARY OF THE INVENTION

The present invention contemplates a method of identifying interventions within a short time frame that mimic the effects of calorie restriction. Such interventions will lead to increased life span, reduce cancer incidence, and/or increase the ago of onset of age-related diseases and tumors.

In a preferred embodiment a method of identifying an intervention that mimics the effects of caloric restriction in cells is disclosed, comprising the steps of:

obtaining a biological sample;

exposing said biological sample to an intervention;

waiting a specified period of time;

assessing changes in gene expression levels, levels of RNA, protein, or protein activity levels related to one or more biomarkers of aging; and identifying said intervention as one that mimics the effects of caloric restriction if one or more changes in said levels also occurs in caloric restriction.

The biological sample may be either in vitro or in vivo. In a preferred embodiment, the biological sample comprises cells. In a more preferred embodiment, the cells are obtained from a mammal. In an even more preferred embodiment, the mammal is a mouse.

In one embodiment, the change in gene expression levels, levels of RNA, protein, or protein activity levels corresponds to a change in gene expression for a gene encoding a chaperone protein. In a preferred embodiment, the chaperone protein is GRP78.

In one embodiment, said biomarker is apoptosis. In another preferred embodiment, said biomarker is aging. In another preferred embodiment, said biomarker of aging is a production of cancer cells.

In a preferred embodiment, the changes in said gene expression level, levels of RNA, protein, or protein activity levels related to one or more biomarkers of aging occur in 6 weeks or less. In a more preferred embodiment, the changes in said gene expression levels, levels of RNA, protein, or protein activity levels related to one or more biomarkers of aging occur in four weeks or less. In an even more preferred embodiment, the changes in said gene expression levels, levels of RNA, protein, or protein activity levels related to one or more biomarkers of aging occur in two weeks or less. In a most preferred embodiment, the changes in said gene expression levels, levels of RNA, protein, or protein activity levels related to one or more biomarkers of aging occur in about two days or less.

In a one embodiment, changes in gene expression are evaluated using a gene chip. In a preferred embodiment, the gene chip contains genes for immune system activation. In another preferred embodiment, the gene chip contains genes for DNA repair. In another preferred embodiment, the gene chip contains genes associated with apoptosis. In another preferred embodiment, the gene chip contains genes for the enteric nervous system.

In an alternate embodiment, the biological sample is a test animal. In a preferred embodiment the disclosed method additionally comprises determining changes in said levels in a reference animal having identifying characteristics of a long-term calorie-restricted animal wherein the reference animal has been on a calorie restricted diet for less than about 6 weeks and wherein said changes are used in said identifying said intervention as one that mimics the effects of calorie restriction. In a more preferred embodiment, the reference animal has been on a calorie restricted diet for less than about 4 weeks. In an even more preferred embodiment, the reference animal has been on a calorie restricted diet for less than about 2 weeks.

In a preferred embodiment, the test animal is a mouse. In a preferred embodiment, changes in gene expression are assessed in the test animal.

In a more preferred embodiment, the disclosed method further comprises:

obtaining a gene expression profile from a calorie-restricted reference animal;

comparing changes in gene expression for the test animal to the gene expression profile of the calorie-restricted reference animal; and identifyng said intervention as one that mimics the effects of calorie restriction if the gene expression profile of the test animal is statistically similar to the gene expression profile of the calorie restricted animal.

In a more preferred embodiment, the gene expression profile of the test animal is determined to be statistically similar to the gene expression of the calorie restricted animal by one-way ANOVA followed by Fisher's test (P<0.05).

In another aspect of the invention, a system is disclosed for identifying an intervention that mimics the effects of calorie restriction in a test animal comprising a test animal and a gene chip comprising genes known to have altered expression during calorie restriction. In a preferred embodiment, the gene chip comprises genes selected from the group consisting of genes for immune system activation, genes for DNA repair, genes associated with apoptosis and genes for the enteric nervous system.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied a carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

These and other feature of this invention will now be described with reference to the drawings of preferred embodiments which are intended to illustrate and not to limit the invention.

Figure 2:
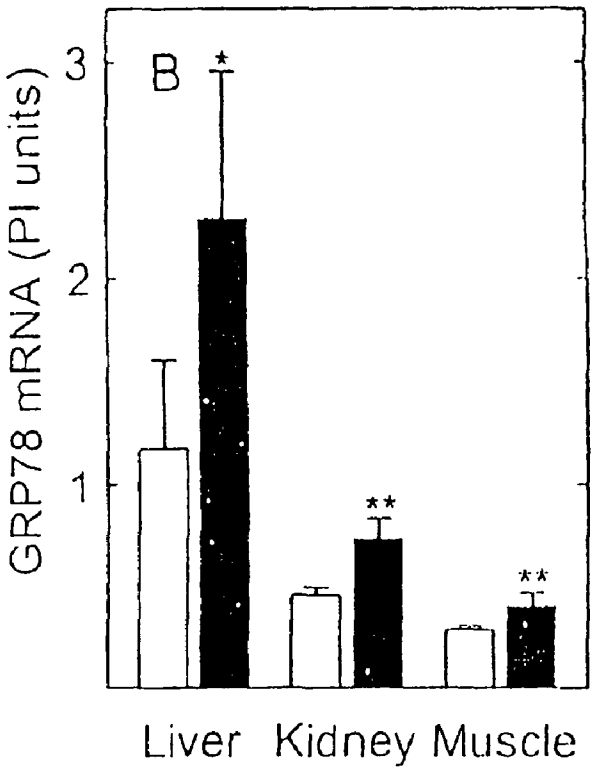
FIG. 2. The gene and tissue specificity of the chaperone feeding response. A, The domain of chaperone genes responsive to feeding was determined by quantifying hepatic chaperone mRNA abundance using RNA from mice fasted for 48 hours (n=6; open bars) or from mice fasted 48 hours, refed and killed) 1.5 h later (n=6; filled bars). The mRNAs were quantified by dot-blotting and Northern blotting. There was no significant difference in the results obtained with either technique. The dot-blotting results are shown. B, Liver, kidney, and muscle GRP78 mRNA from 24-hour fasted mice (n=4), and from 24-hour fasted mice 1.5 hours after feeding (n=5). These data were from different mice than used in panel A. The statistical significance of the results are indicated (*, P<0.05; , P<0.01; *, P<0.001).
Figure 2:
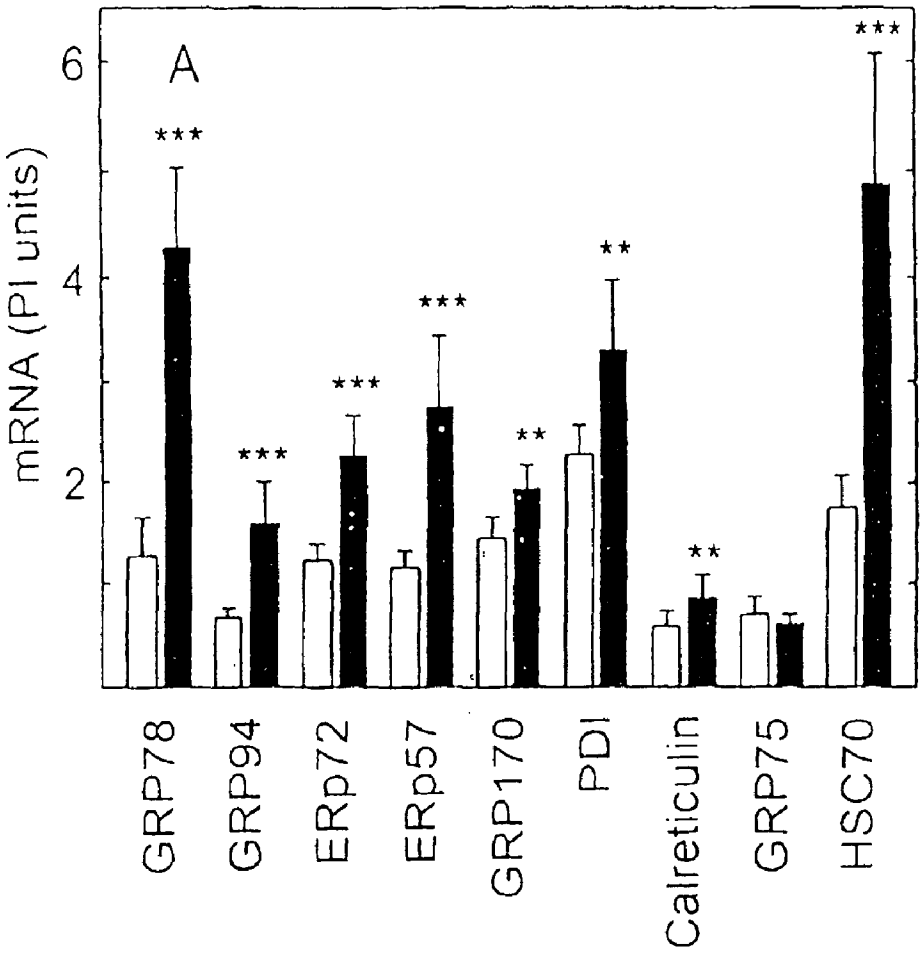
Figure 3:
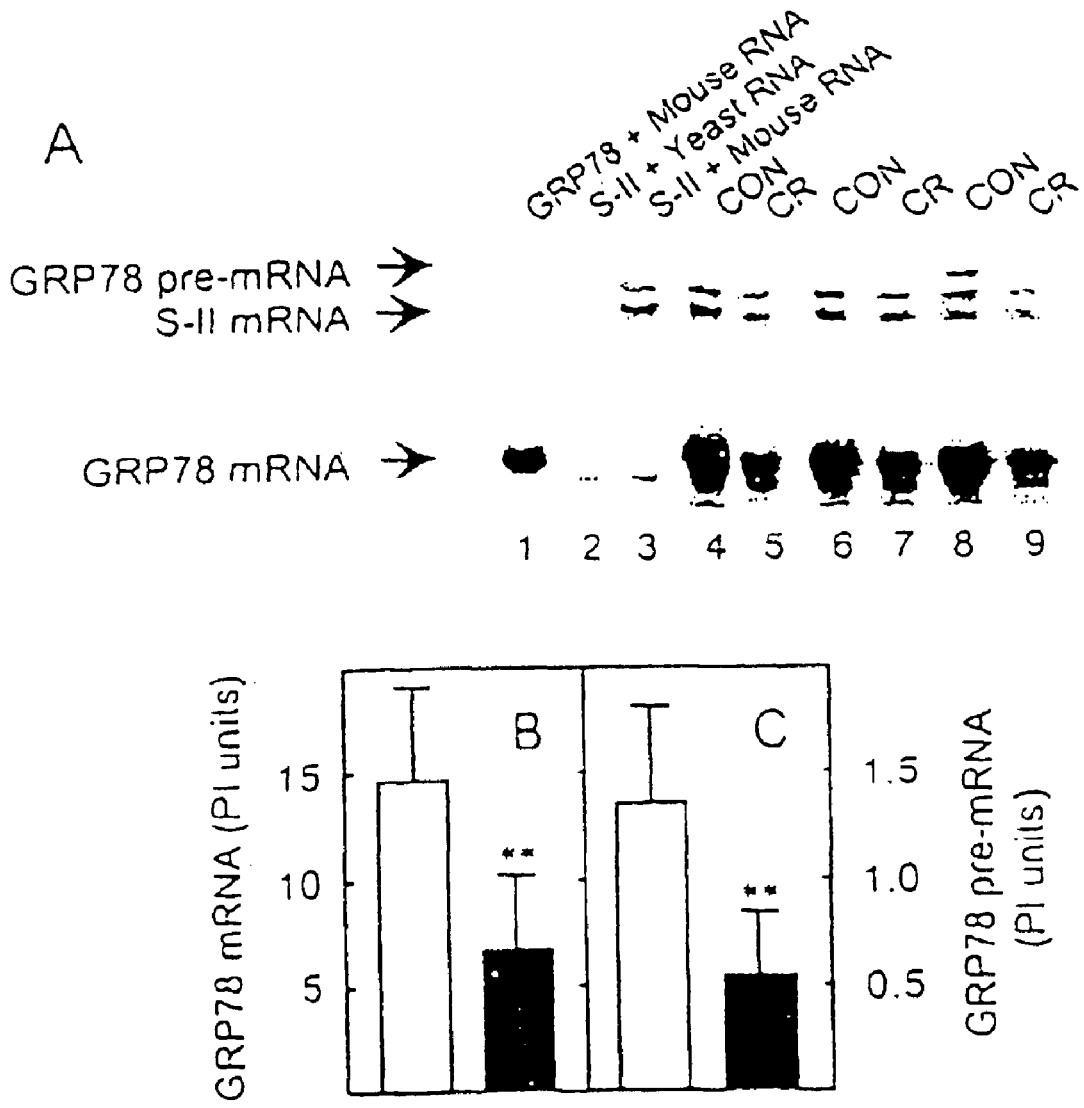
FIG. 3. Effects of CR on hepatic pre-mRNA and GRP78 mRNA abundance. A, RNase protection of pre-mRNA and mRNA in CR and control mice. Hepatic RNA was purified from control and CR mice and hybridized with an RNA probe for transcripts spanning the third intron and fourth exon boundary of the GRP78 gene. The precursor mRNA protected a 223 base region of the probe, labeled GRP78 pre-mRNA, while the GRP78 mRNA protected a 113 base fragment, so labeled in the figure. A probe for S-II mRNA coding sequences was included in each reaction as an internal control. It protected a 185 base fragment labeled S-II mRNA in the figure. Lane 1 shows the protected fragments produced by the GRP78 probe and mouse liver RNA. Lane 2 shows the fragments produced by the S-II probe hybridized to yeast total RNA. Lane 3 shows the results produced by the S-II probe hybridized to mouse liver RNA. Lanes 4, 6, and 8 show the results produced by hepatic RNA from control mice. Lanes 5, 7, and 9 show the results with RNA from CR mice. Quantification of the abundance of the protected fragments representing the GRP78 mRNA (B) and pre-mRNA (C). Studies such as than shown above were conducted using hepatic RNA from 6 CR and 6 control mice. The intensity of the protected fragments was quantified with a phosphorimager. The intensities of the pre-mRNA and mRNA fragments were normalized to the intensity of the protected fragment representing S-II mRNA. Statistical significance is indicated as in the legend to FIG. 2.

The intensity of the protected fragments was quantified and normalized as described in FIG. 3 above. Statistical significance is indicated as in the legend to FIG. 2.

Figure 5:
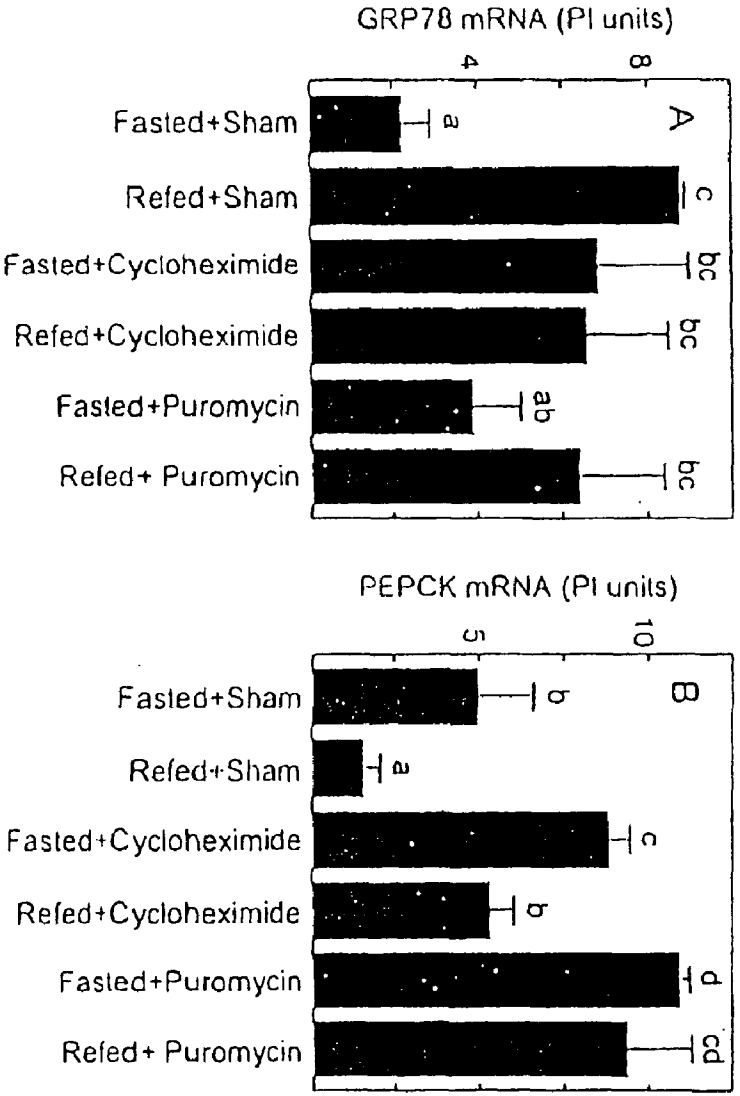

FIG. 5. Effects of protein synthesis inhibitors on the feeding response of GRP78 (A) and PEPCK (B) mRNA. Mice fasted for 48 h were injected i.p. with vehicle and after 1 hour injected a second time i.p with vehicle (Refed+Sham; n=6). Mice fasted for 48 hours were injected i.p. with vehicle 30 min before and 30 min after feeding (Refed+Sham, n=6). Mice fasted for 48 h were injected i.p. with cycloheximide and after 1 hour injected a second time i.p with cycloheximide (Fastest+Cycloheximide; n=6). Mice fasted for 48 h were injected i.p. with cycloheximide 30 min before and 30 min after feeding (Refed+Cycloheximide; n=6). Mice fasted for 48 h were injected i.p. with puromycin and after 1 hour injected a second time i.p with puromycin (Fasted+Puromycin; n=6). Mice fasted for 48 h were injected i.p. with puromycin 30 min before and 30 min after feeding (Refed+Puromycin; n=6). GRP78 and PEPCK mRNA abundance were determined using purified hepatic RNA. Bars without common superscripts are significantly different (P<0.005).

Figure 6:
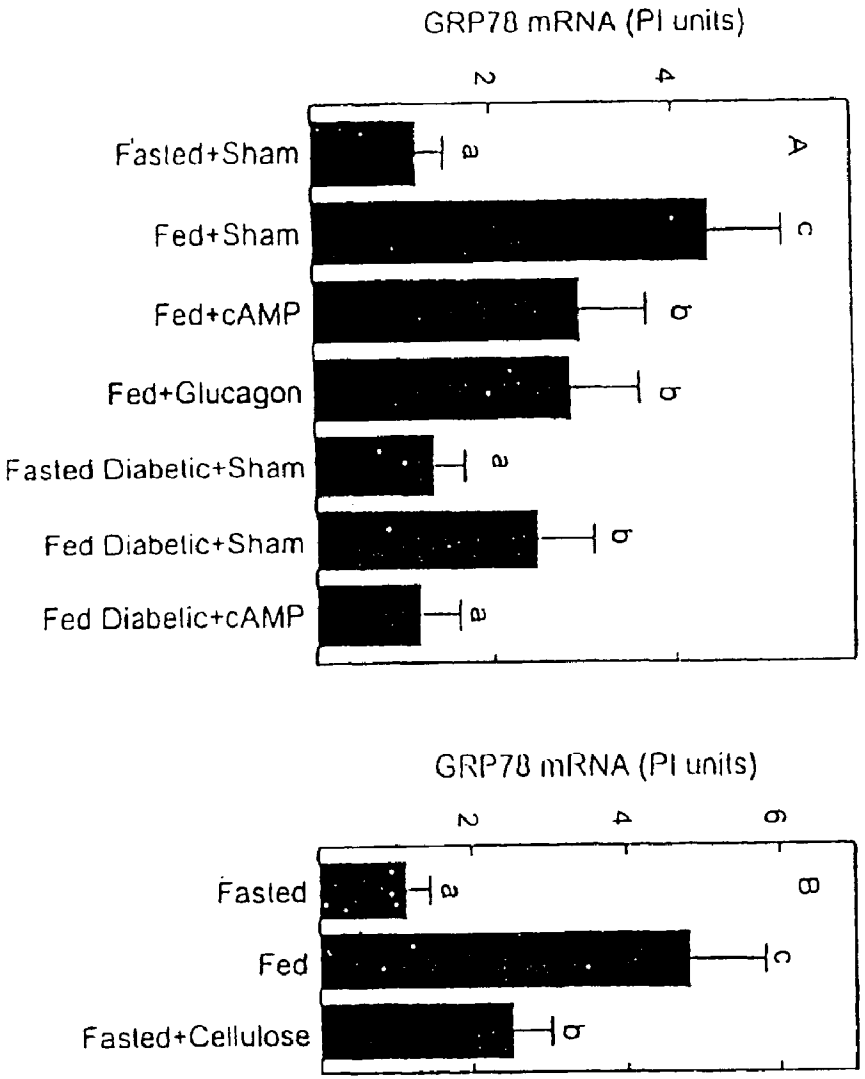

FIG. 6. Regulation of the fasting-feeding response by insulin, dibutyryl-cAMP, glucagon, and ingestion of mineral oil and cellulose. A, Groups of six mice were fasted for 48 h and treated as follows: Fasted+Sham mice were injected with vehicle and 1 h later vehicle injected a second time; Fed+Sham mice were sham injected with vehicle 30 min before and 30 min after feeding; Fed+cAMP mine were injected with dibutyryl-cAMP and theophylline 30 min before and 30 min after feeding; Fed+glucagon mice were injected with glucagon 30 min before and 30 min after feeding; Fasted Diabetic+Sham mice, previously rendered diabetic with STZ, were vehicle injected and 1 h later vehicle injected a second time; Fed Diabetic+Sham, STZ-diabetic mice were sham injected with vehicle 30 min before and 30 min after feeding; Fed Diabetic+cAMP, diabetic mice were injected with dibutyryl-cAMP and theophylline 30 min before and 30 min after feeding. All mice were killed 1 h after their last injection. Total RNA was isolated from the liver and subjected to dot-blot analysis. Bars with no common superscripts are significantly different (P<0.005). B, Effects of mineral oil and cellulose ingestion on liver GRP78 mRNA abundance. Groups of six mice were fasted for 48 h and treated as follows: Fasted, mice were fasted for 48 h and killed; Fed, mice were fasted for 48 h, fed, and killed 1.5 h later; Fasted+cellulose, mice fasted for 48 h were fed a mixture of cellulose and mineral oil, and killed 1.5 h later. Significance is indicated as in the legend to FIG. 5.

Figure 7:
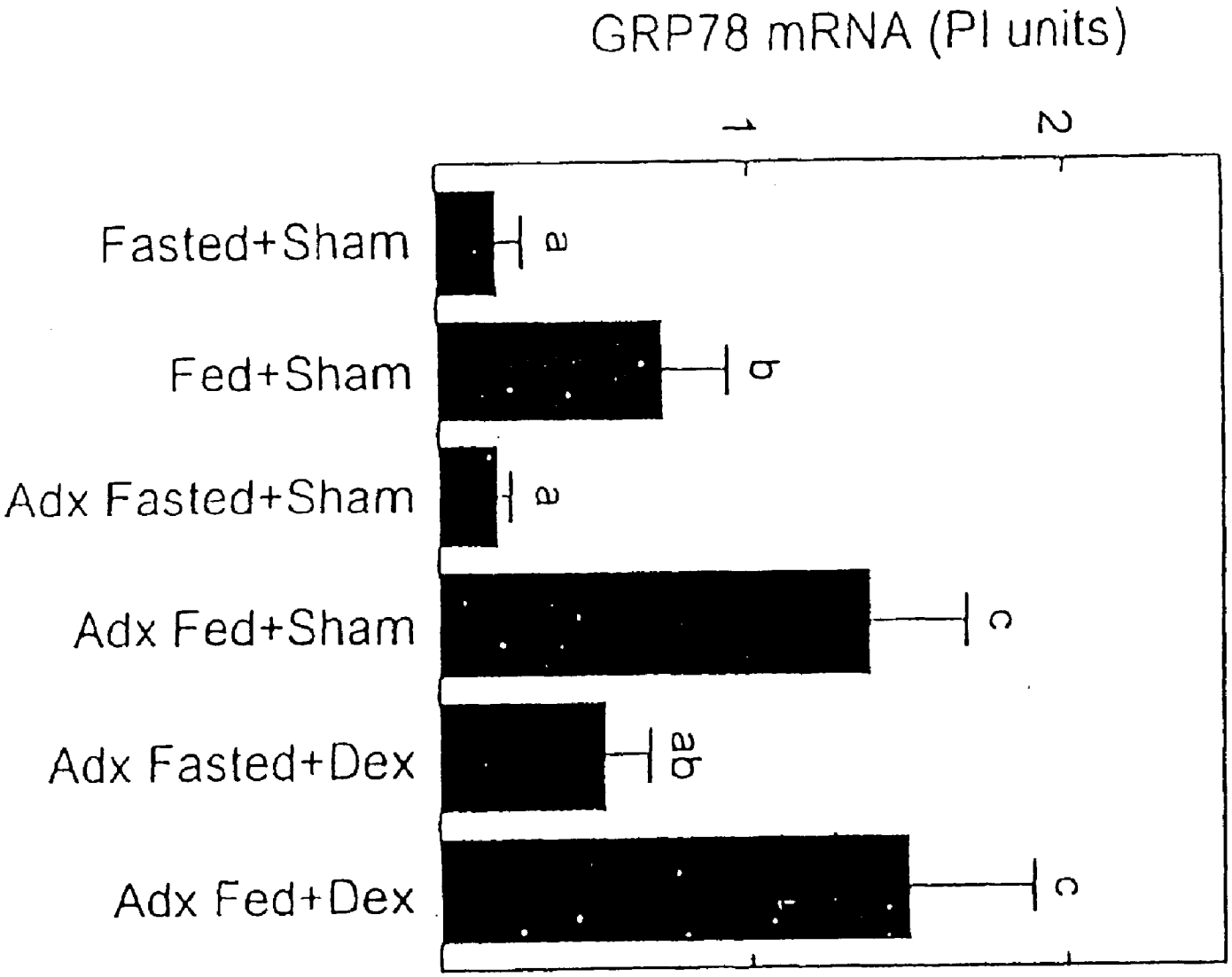

FIG. 7. Effects of adrenalectomy and dexamethasone administration on the expression and regulation of hepatic GRP78 mRNA. Groups of six mice were fasted for 48 h and treated as follows: Fasted+Sham, sham-operated mice were injected with vehicle IP 7.5 h and 1.5 h before they were killed; Fed+Sham, sham-operated mice were injected with vehicle IP 6 hours before and 30 min after feeding, and mice were killed 1 h after the last injection; Adx Fasted+Sham, adrenalectomized mice were injected with vehicle IP 7.5 h and 1.5 h before they were killed; Adx Fed+Sham, adrenalectomized mice were injected with vehicle IP 6 hours before and 30 min after feeding, and the mice killed 1 h later; Adx Fasted+Dex, adrenalectomized mice were injected IP with dexamethasone 7.5 h and 1.5 h before they were killed; Adx Fed+Dex, adrenalectomized mice were injected IP with dexamethasone 6 hours before and 30 min after feeding, and killed 1 h later. Significance is indicated as in the legend to FIG. 5.

Figure 8:
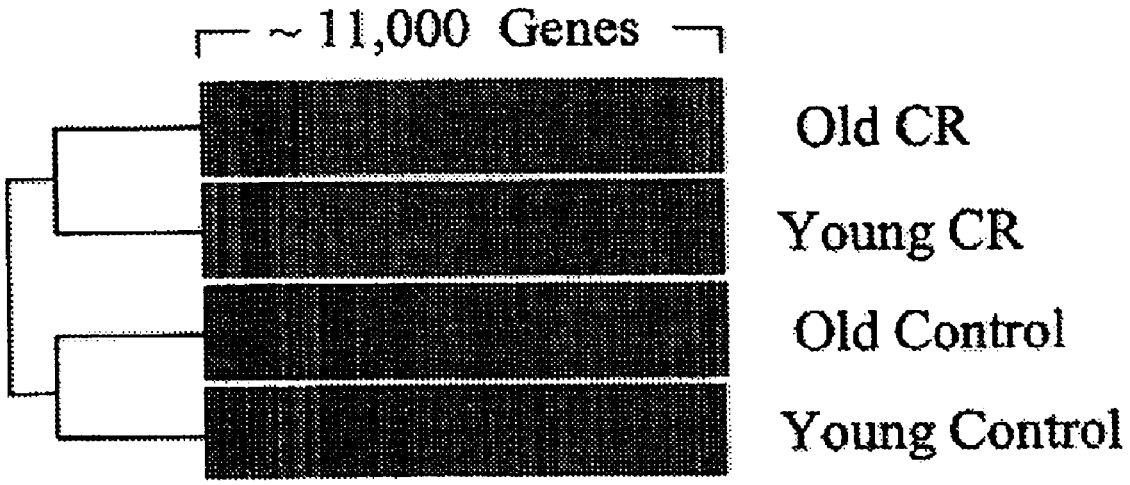

FIG. 8. The hepatic gene expression profiles of old control, old CR, young control, and young CR mice. The mice weighed 37.2+1.9 g, 22.8+1.2 g, 26.0+2.8 g, and 19.4+1.6 g, respectively. The CR groups consumed approximately 50% fewer calories than their control counterparts post-weaning, as described. Levels of specific mRNA were determined using the Mu11KsubA and Mu11KsubB [GeneChip] *GeneChip®* arrays (Affymetrix, Santa Clara, Calif.) containing targets for approximately 12,000 known mouse genes and ESTs. The experiment tree function of GeneSpring 3.0 (Silicon Genetic, San Carlos. Calif.) was utilized to display the results. The horizontal axis represents the position of each gene assigned by the "gene tree" average-linkage hierarchical clustering algorithms of the program. Below the position assigned to each gene is a color-coded indication of its relative expression level, based on a continuous scale. Bright blue indicates no detectable expression, purple average expression, and bright red high expression. The average expression of each gene in each group is shown. The GeneSpring "experiment tree" clustering algorithm calculated an average-linkage hierarchical clustering dendrogram of the data for each group of mice, which is shown to the left of the expression profiles.

Figure 9:
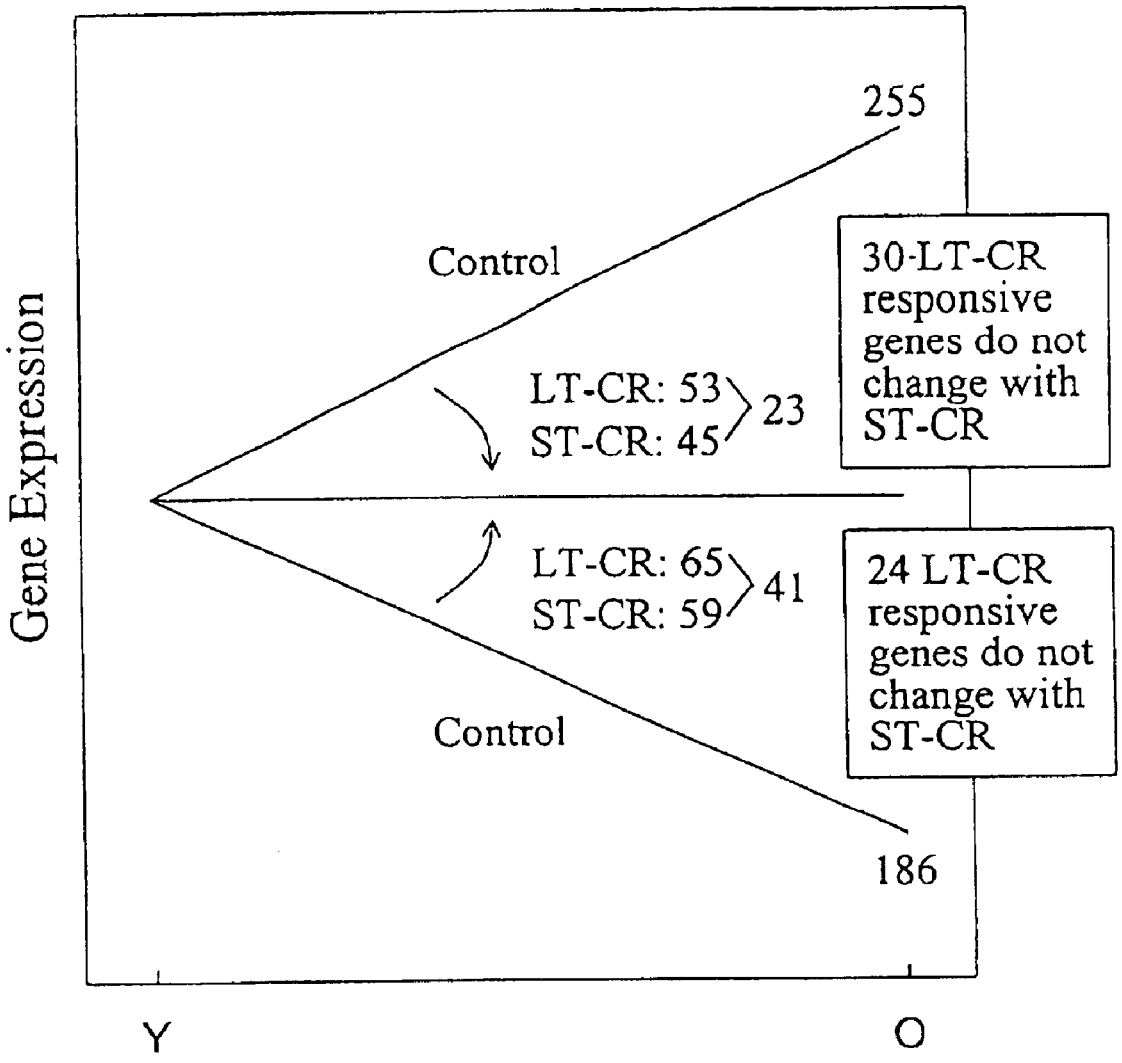

FIG. 9. Schematic representation of the hypothesis that CR acts by preventing age-related changes in gene expression. During aging, some genes become over expressed or under-expressed relative to their levels in young aninals (lower and upper lines). Unchanged expression with age is represented by the horizontal line. These deviations are assumed to be deleterious. The important genes effected by CR, in this hypothesis, are the over- or under-expressed genes returned to youthful levels of expression (arrows). The numbers of genes and ESTs in each category are shown at the ends of the lower and upper lines. The number of known genes in each category returned to baseline expression by LT. and ST-CR are given after the colons. Long-term and short-term CR both acted to reverse or prevent 23 of the increases and 41 of the decreases. Thus, long-term LT-CR actually prevented the increased expression of only 30 genes and ESTs and the decreased expression of only 24 genes and ESTs.

FIG. 10. Avenge of pairwise comparison of the global gene expression correlation coefficient for each possible pair of mice FIG. 11. The hepatic gene expression profiles of young CR, young control and streptozotocin (STZ)-heated mice. Levels of specific mRNA were determined using the Mu11KsubA and Mu11KsubB[GeneChip] *GeneChip®* arrays (Affymetrix, Santa Clara, Calif.) containing targets for approximately 12,000 known mouse genes and ESTs. The experiment tree function of GeneSpring 3.0 (Silicon Genetic, San Carlos, Calif.) was utilized to display the results. The horizontal axis represents the position of each gene assigned by the "gene tree" average-linkage hierarchical clustering algorithm of the program. Below the position assigned to each gene is a color-coded indication of its relative expression level, based on a continuous scale. Bright blue indicates no detectable expression, purple average expression, and bright red high expression. The average expression of each gene in each group is shown. The GeneSpring "experiment tree" clustering algorithm calculated an average-linkage hierarchical clustering dendrogram of the data for each group of mice, which is shown to the left of the expression profiles.

FIG. 12. Average of pairwise comparison of the global gene expression correlation coefficient for each possible pair of mice.

Figure 13:
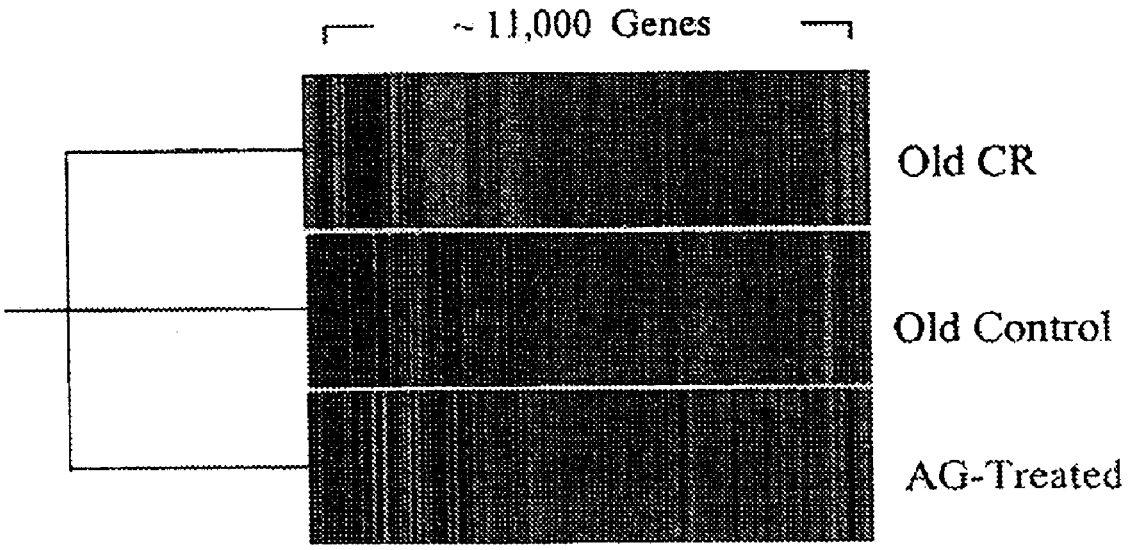

FIG. 13. The hepatic gene expression profiles of old CR, old control and aminoguanidine (AG)-treated mice. Levels of specific mRNA were determined using the Mu11KsubA and Mu11KsubB[GeneChip] *GeneChip*® arrays (Affymetrix, Santa Clara, Calif.) containing targets for approximately 12,000 known mouse genes and ESTs. The experiment tree function of GeneSpring 3.0 (Silicon Genetics, San Carlos, Calif.) was utilized to display the results. The horizontal axis represents the position of each gene assigned by the "gene tree" average-linkage hierarchical clustering algorithm of the program. Below the position assigned to each gene is a color-coded indication of its relative expression level, based on a continuous scale. Bright blue indicates no detectable expression, purple average expression, and bright red high expression. The average expression of each gene in each group is shown. The GeneSpring "experiment treet" clustering algorithm calculated an average-linkage hierarchical clustering dendrogram of the data for each group of mice, which is shown to the left of the expression profiles.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

The effects of long term calorie restriction include increases in the rate of clearance of serum proteins, including glucose damaged serum proteins, from the blood as well as changes in gene expression. For example, long term calorie restriction down regulates the expression of certain chaperone genes, up regulates the expression of certain transcription factors and homeobox genes, increases expression of immune system genes, and increases genes enhancing genetic stability and apoptosis. These changes in gene expression correlate with an increase in apoptosis, reduced cancer incidence and increase the turnover of damaged and toxic serum proteins, reducing kidney and vascular damage with age or diabetes.

Molecular chaperones assist in the biosynthesis, folding, processing, and degradation of proteins. Many of the chaperone genes are stress inducible. Subsets of chaperones are induced by different physiological stressors. For example, the majority of the known endoplasmic chaperones are induced by stresses that produce malfolded or improperly glycosylated proteins in the ER. This unfolded protein response pathway also may adjust the level of protein trafficking through the ER to the level of ER chaperones. Other chaperones, such as the abundant cytoplasmic chaperone HSC70 are normally thought of as constitutively expressed. The present invention is based in part on the finding that certain chaperone genes are down regulated by calorie restriction (such regulation is thought to be mediated through the insulin and glucagon pathways). The expression of Erp72, Erp57, GRP 170, GRP78, GRP94, HSC70, Calnexin, and Calreticulin are particularly affected by calorie restriction.

The fasting mRNA and protein levels of nearly every ER chaperone studied were found to be significantly and consistently reduced in the livers of CR mice chronically fed a low caloric diet. In the case of GRP78, levels decreased by approximately 66%. Further, the reduction in chaperone mRNA levels was proportional to the reduction in calorie consumption. The fewer calories consumed, the lower the level of chaperone mRNA. We subsequently found that fasting chaperone mRNA levels changed over the course of 2 weeks in response to different levels of chronic calorie consumption. The more calories consumed per week, the higher the chaperone levels. Chaperone mRNA levels respond more rapidly to calorie consumption.

mRNA for most ER chaperones, and for the major cytoplasmic chaperone, HSC70, are dynamically responsive (within 1.5 h) to each meal, and to the number of calories consumed. Features of this induction distinguish it from the unfolded protein response. The feeding induction was observed in kidney and muscle tissue, as well as in the liver. Postprandial changes in glucagon, in conjunction with insulin, were found to be the key mediators of this induction.

Chaperone mRNA abundance responds within 1.5 h to caloric intake. Insulin and glucagon may be important for the response. This feeding response is rapid. By 1.5 hours after feeding, ER chaperone mRNAs were at or near their maximum level of induction. This feeding-related induction is not limited to one strain of mouse or to one species. Further, the response is found in tissues other than liver. Thus, it is a response which is generally important to the physiology of a variety of cell types in vivo.

Because many chaperones are relatively stable proteins, their protein levels change more slowly in response to caloric intake than their mnRNAs. For example, GRP78 protein has a half-life of over 24 hours in cultured cells. We found that GRP78 protein levels change only over a span of several days in response to changes in average daily calorie consumption. In this way, many chaperones may effectively integrate the rapid mRNA responses to feeding into longer term changes in chaperone protein levels. Long term differences in average calorie consumption do lead to differences in the hepatic levels of both ER and some cytoplasmic chaperones.

RNase protection assays indicate that GRP78 mRNA is transcriptionally regulated in response to feeding. Similar RNase protection results were obtained with hepatic RNA from chronically CR mice. Thus, both feeding and CR transcriptionally alter the expression of the chaperone genes.

Puromycin led to partial induction of GRP78 mRNA. It is unlikely that induction of the mRNA by cycloheximide is due to stabilization of the transcript by polysome aggregation. While cycloheximide protects some mRNAs from inactivation and degradation in this way, puromycin does not. Rather, it inhibits translation by polysome dissociation. Thus, maintenance of low hepatic GRP78 mRNA levels most likely requires the action of an unstable repressor of GRP78 gene expression in fasted mice. In the presence of inhibitors of translation, this repressor may decay, releasing the gene from repression.

Second, there was no augmentation of GRP78 mRNA induction when feeding and inhibition of translation were combined. While partial induction of the mRNA was found in puromycin treated mice, feeding induced the mRNA to the same level found in the absence of the inhibitor. Further, cycloheximide induced the mRNA to the same extent. Without being bound to any particular mechanism, it is suggested that the inhibitors and feeding may induce the gene through a common pathway.

Third, since feeding fully induced GRP78 mRNA in puromycin treated mice, de nova protein synthesis is not required for the feeding response. Preexisting signaling and regulatory factors mediate the response. Fourth, the feeding response cannot result from a postprandial increase in protein trafficking through the ER. Enhanced ER de novo protein trafficking an induce chaperone mRNA. However, no such increase could have occurred in the presence of puromycin.

Fifth, the unfolded protein and growth factor responses are not involved in the induction of chaperones by feeding. Cycloheximide blocks the unfolded protein and growth factor responses. We are aware of only one manipulation besides feeding capable of inducing ER chaperone mRNA in the presence of cycloheximide. GRP mRNAs are induced by cellular hypoxia in culture, and this induction is independent of cycloheximide treatment. Whether the feeding and hypoxia response share common molecular pathways is unknown at present.

Feeding is well-known to decrease glucagon and increase insulin levels. Both glucagon and dibutyryl-cAMP blunted the feeding induction of GRP78 mRNA. Thus, glucagon is a negative regulator of GRP78 expression in vivo. The feeding induction of GRP78 mRNA was significantly reduced in STZ-diabetic mice. Without being bound to any particular mechanism, this result and the absence of a feeding response in STZ-diabetic, dibutyryl-cAMP-treated mice indicate that the action of both hormones is required for the response.

Other effectors which are known to respond to feeding were also examined. Luminal stimuli can promote the release of gastrointestinal hormones. For this reason, we determined whether luminal filling with a non-digestible mixture of mineral oil and cellulose could stimulate chaperone expression. A small but significant response was found. However, insulin and glucagon have a much stronger effect on chaperone mRNAs, indicating they are the signals primarily responsible for the feeding response.

The feeding response was enhanced in adrenalectomized mice. These results suggest that other adrenal hormones, perhaps catecholamines, may partially blunt the chaperone mRNA response to feeding. However, the mechanism by which these hormones stimulate the feeding response is unknown at present.

Overall, feeling rapidly and strongly induced the mRNA for the major cytoplasmic chaperone, HSC70, and most ER chaperones examined. Feeding also induced BR chaperone mRNAs in at least three different tissues. Feeding and CR regulated chaperone mRNA abundance at the transcriptional level. Without being bound to any particular mechanism, feeding appeared to release chaperone gene expression from the effects of an unstable inhibitor. Insulin was required, and glucagon and cAMP mediated the feeding response. Postprandial changes in glucagon levels may be the primary mediator of the response. Gastrointestinal and adrenal hormones, but not glucocorticoids also have a role in the feeding response.

Surprisingly, changes in gene expression are also observed with short-term calorie restriction. These changes is gene expression are virtually identical to the changes observed in long-term CR. Short-term calorie restriction occurs when switching a mature test animal to a diet which is about 50% less than a control diet for about 2–6 weeks. In a preferred embodiment, the test animal is a mature mouse and the mature mouse is switched to a calorie-restricted diet at about 31 months. Preferably, as intermediate diet which is about 20–40% less than a control diet is employed for about two weeks before switching to a CR diet for an additional two weeks.

Both long term and short-term CR produces its profound effects on mammalian physiology by affecting the expression of genes. To identify as broadly as possible the effects of caloric restriction on global patterns of gene expression, gene chip technology was utilized to characterize the effects of long and short term CR on the expression of approximately 11,000 mouse genes in the liver.

Liver is an attractive organ for study, since it contains a number of cell types, allowing assessment of the effects of CR on hepatocytes, which are primarily responsible for the regulation of metabolism and blood sugar, neurons of the enteric nervous system, immune system cells in the blood, and vascular smooth muscle cells, among others. In liver, by far the predominant effect of caloric restriction is the activation of gene expression. In addition, after only four weeks of caloric restriction, the gene expression profile of old mature mice had been shifted from the profile characteristic of fully fed "normo-aging" mice to the gene expression profile of slow aging, long term CR mice. In both long and short-term CR mice, changes were observed in gene expression of immune system genes, genes enhancing genetic stability and apoptosis, genes of the enteric nervous system and liver specific genes.

The methods of the present invention include the identification of interventions that mimic the effects of calorie restriction. Particularly contemplated by the invention are methods of identifying interventions that have as effect on life span, aging, and/or the development of age-related diseases and cancer.

In certain embodiments, such methods comprise obtaining cells, exposing them to an intervention, and observing whether the intervention affects the gene expression profile, levels of RNA, protein, or protein activity related to one or more biomarkers of aging. Preferably, such changes in gene expression, RNA, protein, or protein activity levels would occur within four weeks of the intervention. More preferably, such changes would occur within two weeks of the intervention, and most preferably, such changes occur within two days of the intervention. Such methods permit the identification of pharmacological or other means of achieving a metabolic state similar to the profile observed with long and short-term CR.

The methods of the present invention include the use of in vitro assays (including gene chip assays) as well as animal assays. Preferably, however, the methods are carried out in live mammals. For example, transgenic mice having enhanced chaperone expression may be used to measure an intervention's ability to reduce cancer, apoptosis, and/or life span. Alternatively, the present methods may be used to identify interventions that mimic calorie restriction simply by measuring the intervention's ability to alter gene expression for a particular gene or set of genes in live mammals. Such methods allow identification of effective interventions in a short period of time. Interventions identified by the methods of the present invention may be pharmacological, surgical or otherwise. Combinatorial chemistry may also be used in order to screen a large number of pharmacological compounds. In general, the interventions identified by the present invention should be effective in the treatment of cancer, diabetes, age-related diseases and/or the extension of life span.

While the described embodiment represents the preferred embodiment of the present invention, it is to be understood that modifications will occur to those skilled in the art without departing from the spirit of the invention. The scope of the invention is therefore to be determined solely by the appended claims.

EXAMPLES

Example 1

Long Term Calorie Restricted (LTCR) Animals and Treatments for Chaperone Studies Female, 28-month old mice of the long-lived $F_1$ hybrid strain C3B10RF$_1$ have been described previously. Mice were weaned at 28 d, housed individually and subjected to one of two diets. The control diet consisted of casein (high protein), 207.0 g/kg, DL-methionine, 4.0 g/kg, dextrose monohydrate, 301.8 g/kg, corn starch, 290.0 g/kg, cellulose, 702. g/kg, brewer's yeast, 8.0 g/kg, Harlan Teklad Vitamin Mix #40060, 10.0 g/kg, Harlan Teklad AIN-76 Mineral Mix #170915, 35.0 g/kg, calcium carbonate ($CaCO_3$), 3.0 g/kg, magnesium oxide (MgO), 1.0 g/kg, sodium fluoride (NaF), 2.3 mg/kg, sodium molybdate ($Na2MoO.2H_2O$), 0.5 mg/kg. The 50% restricted diet consisted of casein (high protein), 362.0 g/kg, DL-methionine, 7.0 g/kg, dextrose monohydrate, 172.03 g/kg, corn starch, 153.1 g/kg, cellulose, 83.6 g/kg, brewer's yeast, 14.0 g/kg, Harlan Teklad Vitamin Mix #40060, 17.5 g/kg, harlan Teklad AIN-76 Mineral Mix #170915, 61.25 g/kg, calcium carbonate ($CaCO_3$), 5.25 g/kg, magnesium oxide (MgO), 1.75 g/kg, sodium fluoride (NaF), 3.0 mg/kg, sodium molybdate ($Na2MoO.2H_2O$), 0.9 mg/kg. From weaning, control mice were fed 4.8 g of the control diet on Monday through Thursday. On Friday they were fed 13.8 g of control diet. This feeding regimen provided 450 kJ/wk. From weaning, the 50% calorie restricted (CR) mice were fed 4.6 g of the restricted diet on Monday and Wednesday, and 6.9 g on Friday. This regimen provided 225 kJ/wk. Each dietary group received approximately equal amounts of protein, corn oil, minerals and vitamins per gram body weight. The amount of carbohydrates consumed varied between groups. Beginning 30 d before these studies, the control mice were fed 4.1 g (54.44 kJ) control diet daily at 0900 h. The 50% restricted mice were fed 2.3 g of restricted diet (32 kJ) daily at 0900 h. During this 30 d period, the control and restricted mice received approximately 15% and 50% less dietary energy than normally thought to be required for a typical mouse {Subcommittee on Laboratory Animal Nutrition & Committee on Animal Nutrition 1978 ID: 5480} All food was routinely consumed within 30 min.

Retired male Swiss-Webster breeder mice were purchased from Jackson Laboratories. Beginning 30 days before the studies, the mice were fed Monday and Wednesday 11 g and Friday 16.6 g of the control diet daily at 0900 h. In fasting-feeding studies, mice were deprived of food for 48 h, fed 5.5 g of the control diet at 0900 h, and killed 90 min later. The food was consumed within 30 min. Diabetes was induced by three weekly intraperitoneal injections of streptozotocin [10 mg/100 g body weight (b.w.)] in 50 mM sodium citrate, pH 4.5. Mice were diabetic one week after the last injection. Only mice with blood glucose level higher than 3 mg/ml were used. Mice injected with equivalent volumes of sodium citrate served as controls for the STZ-diabetic mice. Adrenalectomized and sham-operated mice were purchased from Jackson Laboratories. Dibutyryl cAMP (Sigma; 18 mg. 100 g b.w.), and theophylline (Sigma; 3 mg/100 g b.w.), glucagon (Sigma; 300 μg/100 g b.w.), dexamethasone (Sigma; 125 μg/100 g b.w), cycloheximide (Sigma; 4 mg. 100 g b.w.), and puromycin (Sigma; 10 mg.100 g b.w.), were administered intraperitonealy to mice as specified in the figure legends. Mice received two doses of each drug or drug combination. The first injection was administered 30 min before feeding, and the second injection was administered 30 min after feeding. Mice were killed 1.5 h after the start of feeding. Drug-injected mice consumed similar amounts of food as control animals during the feeding period. All animal use protocols were approved by the institutional animal use committee of the University of California, Riverside.

Example 2

RNA Isolation and Quantification for Chaperone Studies

Mice were killed and the livers, kidneys, and muscle were removed. Muscle from the hind legs and back was removed and pooled for each animal. Tissues were flash frozen in liquid nitrogen. Approximately 0.2 g of frozen tissue was homogenized for 40 s in 4 ml of TRl Reagent (Molecular Research Center, Cincinnati, Ohio) using a Tekmar Tissuemizer (Tekmar, Cincinnait, Ohio) at a setting of 55. RNA was isolated as described by the TRI Reagent supplier. RNA was resuspended in FORMAzol (Molecular Research Center) and Northern and dot blots were performed using 20 and 10 μg of RNA respectively. The RNA was analyzed using Northern blots to verify its integrity. Dot blots were used to quantify mRNA levels (24; 27). Specific mRNA levels were normalized to the level of total RNA and/or mRNA present in each sample using hybridization with radiolabeled complementary DNA to 18S rRNA and/or transcription factor S-II, as indicated in the figure legends (12; 27). The murine ERp72 2.5 kb cDNA was excised with BamHI from pcD72-1 (19). The 1235 bp murine GRP75 coding fragment was excised with HindIII from pG7z-PBP1.8 (6). A 1.5 kb coding fragment of GRP78 cDNA was produced by digestion of p3C5 with EcoRI and PstI (15). A 1.4 kb hamster GRP94 coding fragment was produced by EcoRI and Sa/K digestion of p4A3 (15). A 664 bp coding fragment of rat calreticulin (nucleotides 148 to 812) was produced by PCR from GT10.U1 (23). The entire 2.4 kb cDNA of murine PDI was excised from pGEM59.4 with Sacl and BamHII (19). A 1 kb coding fragment of hamster GRP170 cDNA was excised with EcoRI and XhoI from pCRmII (16). The 1.9 kb cDNA of murine ERp57 was excised with HindIII and Sstl from pERp61 (18). The 1 kb cDNA of murine HSC70 was excised with PstI from phsc1.5 (9). The 1.3 kb PEPCK coding fragment was produced by SphI followed by SalI digestions of pGEM5ZEP (a gift from Dr. Ganner D. K. Vanderbilt University School of Medicine, Nashville, Tenn.). The fragments were isolated by agarose gel electrophoresis and radioactively labeled using a "QuickPrime Kit (Pharmacia) according to the manufacturer's instructions.

Example 3

RNase Protection Assays for Chaperone Studies

A 223 base pair (bp) DNA fragment made up of 110 bases of intron 3 and all 113 bases of exon 4 of the mouse GRP78 gene was synthesized by PCR using genomic DNA as template and inserted into pT7/T3 (Ambion, Austin, Texas). Two probes of the junction region of intron 7 and exon 7 of the GRP78 gene were produced by PCR using mouse genomic DNA as template. A 257-base fragment including all of exon 7 and the first 113 bases of intron 7 was produced. A 200-base fragment including all of exon 7 and the first 56 bases of intron 7 also was produced. The T7 RNA polymerase promoter was ligated to these PCR fragments using a Lig'nScribe kit as described by the supplier (Ambion). These constructs were used as template for the synthesis of [$^{32}$P]-labeled antisense RNA probes using a MAXIScript kit as described by the supplier (Ambion). RNase protection assays were performed using an RPA II kit as described by the supplier (Ambion). Hybridization of the 257-base RNA probe with GRP78 pre-mRNA protected all 257-bases corresponding to exon 7 and the first 113 bases of intron 7. Hybridization of the 200-base RNA probe to pre-mRNA protected 200-bases corresponding to all of exon 7 and the first 56 bases of intron 7. Hybridization of either probe to GRP78 mRNA protects the 143-bases complementary to exon 7. A 185- and a 277-bp cDNA fragment of S-II cDNA was synthesized and subcloned into pT7/T3 (12). [$^{32}$P]-labeled RNA probes for the sense and antisense transcripts were synthesized in vitro and RNase protection assays performed. Hybridization with S-II mRNA protected the entire 185- or 277-base region of the probes. Protection of only the sense strand probes was detected. Quantitation of the hybridized fragments was determined with ImageQuaNT (Molecular Dynamics, Sunnyvale, Calif.).

Example 4

Plasma Glucose and Insulin for Chaperone Studies

Plasma glucose, insulin, and glucagon concentrations were determined using Glucose [HK] 10 (Sigma, St. Louis, Mo.), Rat Insulin RIA and Glucagon RIA kits (Linco Research, St. Charles, Mo.), as described by the suppliers.

Example 5

Statistical Analysis for Chaperone Studies

Figure 1:
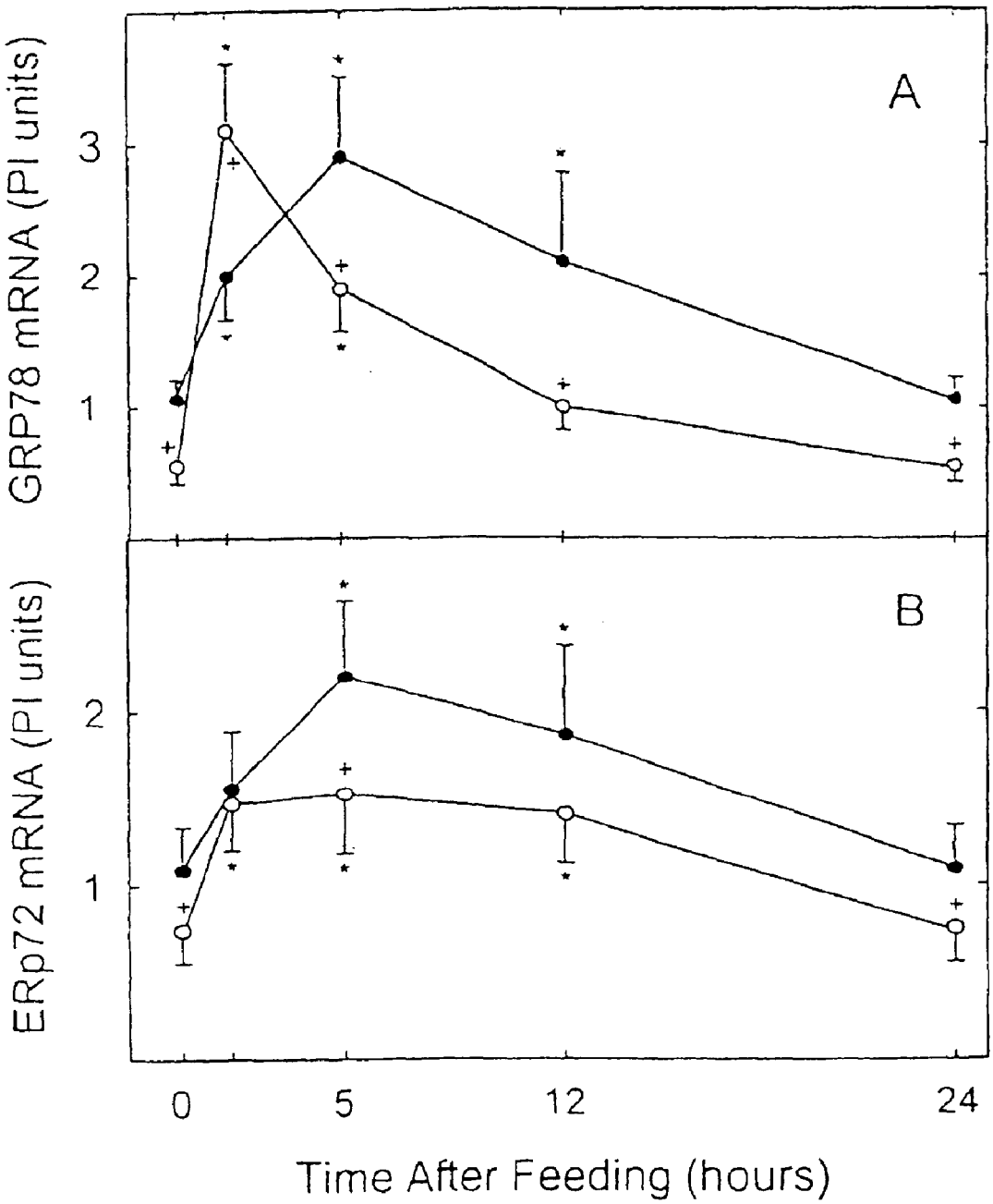
FIG. 1. Effects of feeding on hepatic GRP78 and ERp72 mRNA. At 0, 1.5, 5 and 12 h following feeding, 5 mice from each dietary group were killed. Their weights after 24 h of fasting were 22.96±1.49 for CR and 37.12±1.19 g for control mice. GRP78 mRNA (A) and ERp72 mRNA (B) from control (closed circle) and CR (open circle) mice were quantified using dot-blots. RNA loading and transfer were normalized using data obtained from serial probings for 18S ribosomal RNA and S-II mRNA. Similar results were obtained with both control probes. CR and control mice, fed once daily for 30 days, were fasted for 24 hours and killed (n=5, 0 time point) or refed and killed at the times specified (n=5 for each time point). + represents P<0.01 significance of difference between CR and control at each time point. * represents P<0.01 significance of difference from the 0 time point within each dietary group. The 0 and 24 hour times points are the same data set.

The data shown in FIG. 1 are expressed as means±SD for 5 mice at each time point. The effects of food deprivation and subsequent feeding on mice of each dietary group were analyzed using a one-way ANOVA followed by Fisher's test. The analysis determined whether individual time point means differed from time 0 means within each dietary group. It also determined the differences between the means of the control and CR groups at each time point. Differences of $P<0.05$ were considered significant. Values are expressed as means±SD. Significance was determined with either Student's unpaired t-test ($P<0.95$) or a one-way ANOVA followed by Fisher's or Tukey's tests ($P<0.01$). All statistical analyses were performed with Minitab Statistical Software (Minitah, State College, Pa.).

Example 6

Chronic and Acute Effects of Calorie Consumption on Hepatic Chaperone mRNA

Feeding of the fasted mice rapidly induced the abundance of GRP78 and ERp72 mRNA (FIGS. 1A and 1B). A large increase in chaperone mRNA was detected by 1.5 h after feeding, the first time point studied. The 24-h fasting levels (0 time) of GRP78 and ERp72 mRNA were lower in the CR mice. The response to feeding was kinetically different in control and CR mice. Thus, the amount of food consumed affects the kinetics of the response. The integrated level of GRP78 and ERp72 mRNA over the entire 24-hour period was also less in the CR than in control mice. Similar results were obtained when the effects of feeding on HSC70, ERp57, and calreticulin mRNA were determined (data not shown). Thus, this represents a common response of chaperone gene expression to feeding.

Example 7

Fasting-Feeding Induced Multiple Chaperone mRNAs in Multiple Tissues

Mice were fasted for 48 hours and refed for 1.5 hours. Hepatic GRP78 mRNA was induced approximately 3-fold after this time (FIG. 2A). The mRNA for the other ER chaperones investigated, ERp57, ERp72, GRP94, GRP170, PDI, and calreticulin, and for the most abundant cytoplasmic chaperone, HSC70, also were induced by feeding (FIG. 2A). HSC70 was induced by nearly 3-fold. No changes in the mitochondrial chaperone GRP75 was detected in this study. By examining chaperone levels in other tissues of fasted and fed mice, we found that the feeding-related chaperone induction extends to at least kidney and muscle (FIG. 2B). GRP78 mRNA induction is shown in the figure (FIG. 2B). HSC70 mRNA was also induced in these tissues (data not shown). In studies not shown, we have found that a similar induction of hepatic chaperone mRNAs occurs in rat. Thus, the response is shared by other species.

Example 8

CR Reduces the Abundance of the GRP78 Primary Transcript

RNase protection studies were used to investigate the responsiveness of the GRP78 mRNA and primary transcript to chronic differences in dietary calorie consumption. A probe was utilized for these studies designed so that the GRP78 primary transcript protected a 223 base RNA fragment representing the third intron-fourth exon boundary of the transcript (FIG. 3A lane 1, upper band). The mRNA protected a 113 base fragment of the probe which represents the fourth exon of the gene (FIG. 3A , lane 1, lower band). Much less of the 223 and 113 base GRP78 precursor and mRNA probes were protected by RNA from CR mice (FIG. 3A , lanes 4–9). A probe for 185 bases of S-II mRNA was included in each sample as an internal control (FIG. 3A, lane 3). S-II mRNA is unresponsive to CR or fasting-feeding (25). The unlabeled bands in FIG. 3 represent RNase-resistant artifacts of the S-II probe (FIG. 3A , lane 2).

When the amount of protected probe was quantified and normalized to the signal obtained from the S-II probe, it became clear that the abundance of the chaperone precursor and mRNA were decreased to the same extent in the CR mice (FIG. 3B). The same conclusion was reached using a probe for the boundary regions of intron 7 and exon 7. Consequently, CR decreases either the rate of GRP78 gene transcription or the stability of the GRP78 primary transcript. The data are not consistent with blocked or paused GRP78 gene transcription or changes in the stability of the mRNA in CR mice.

Example 9

Fasting-feeding Induction of the GRP78 Primary Transcript

Figure 4:
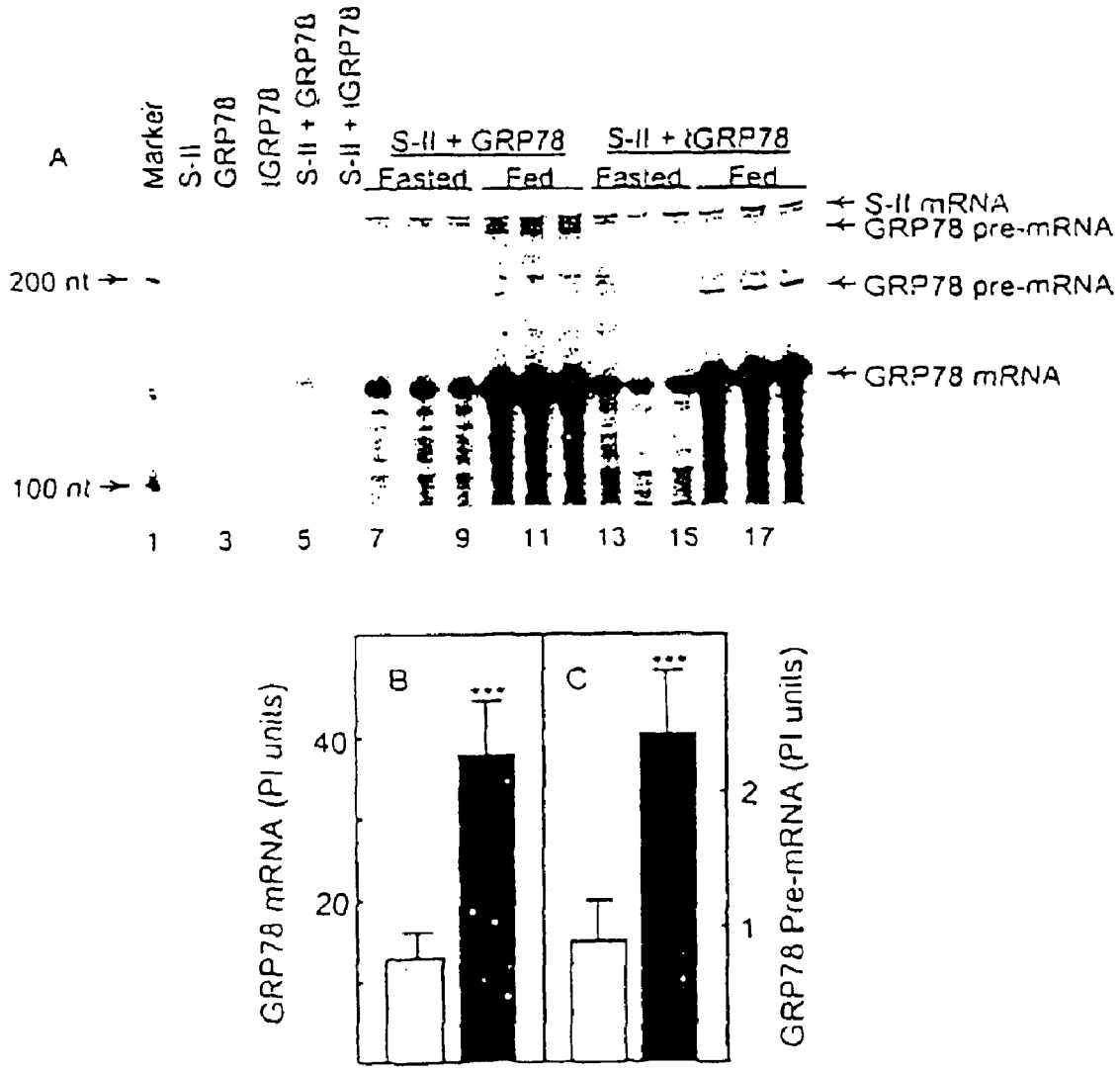
FIG. 4. Effects of feeding on hepatic GRP78 mRNA and pre-mRNA abundance. A, RNase protection of probes for hepatic GRP78 pre-mRNA and mRNA in mice after 48 hours of fasting (n=5), or 1.5 h after feeding of 48-hour fasted mice (n=5). RNA purified from liver was hybridized either to a probe for primary transcripts containing the exon 7 and intron 7 boundary of the GRP78 gene which produced a 257 base protected fragment (labeled S-II+GRP78; lanes 7–12), or to a probe for primary transcripts spanning the exon 7 and intron 7 boundary, which protected a 200 nucleotide fragment (labeled S-II+tGRP78, lanes 13–18), as indicated in the figure. GRP78 mRNA produced a 143 nucleotide fragment representing GRP78 mRNA, as indicated in the figure. A probe for S-II mRNA coding sequences was included in each reaction as an internal control. With this probe, S-II mRNA protected a 277 nucleotide fragment, labeled S-II mRNA in the figure. Lane 1, RNA markers. Lanes 2–6, hybridization of the indicated probes with yeast tRNA. Lanes 7–12, hybridization of the GRP78 and S-II probes with RNA from fasted (lanes 7–9) and refed (lanes 10–12) mice. Lanes 13–18, hybridization of tGRP78 and S-II probes with RNA from fasted (lanes 13–15) and refed (lanes 16–18) mice. Quantification of the abundance of the protected fragments representing the GRP78 mRNA(B) and pre-mRNA (C). Studies such as those shown above were conducted using hepatic RNA from 6 CR and 6 control mice.

RNase protection studies also were used to investigate the fasting-feeding response. RNA isolated 1.5 h after feeding protected much more of a 257 base fragment representing the exon 7-intron 7 boundary of the primary transcript than RNA isolated from fasted mice (compare FIG. 4A, lanes 10–12 to lane 7–9). Similar results were obtained with a probe in which 200 bases representing the exon 7-intron 7 boundary were protected (compare FIG. 4A , lanes 16–18 to lanes 13–15). In each case, RNA from refed mice also protected more of the 143 base fragment representing the exon 7 region of the mRNA (FIG. 4A). A probe for 277 bp of the S-II mRNA was present in each assay for use as an internal control.

Quantification of these data, and normalization of the S-II internal control demonstrated that the mRNA and the precursor RNA were induced by feeding to essentially the same extent (FIGS. 4B and 4C). Similar results were obtained using the probe described earlier for the third intron-fourth exon boundary of the gene (data not shown). Without being bound to a specific mechanism, these data suggest the same molecular step is responsible for regulating the genetic responsiveness of chaperones to both acute and chronic changes in calorie consumption. This mechanism appears to involve changes in either the transcription or the stability of the primary transcript.

Example 10

Inhibitors of Protein Synthesis

To investigate the physiological basis for the fasting-feeding response, studies were performed using inhibitors of protein synthesis. Fasted mice were treated with a dose of cycloheximide or puromycin sufficient to inhibit greater than 95% of protein synthesis in the liver. Treatment with cycloheximide strongly induced GRP78 mRNA in fasted mice (FIG. 5A). GRF78 mRNA also was strongly induced in cycloheximide-treated, refed mice. Puromycin treatment modestly induced GRP78 mRNA in fasted mice (FIG. 5A). Feeding of puromycin treated mice fully induced the mRNA. Thus, induction by feeding does not appear to require de novo protein synthesis. Further, these results suggest that the lower chaperone mRNA levels in fasted mice may involve the action of a rapidly turning over factor.

The effects of the protein synthesis inhibitors on PEPCK mRNA also was determined as a positive control. The effects of fasting-feeding and cycloheximide treatment on this mRNA are well known. Fasting induced, and feeding repressed PEPCK mRNA, as expected (FIG. 5B). Also, as expected from published data, cycloheximide increased PEPCK mRNA in both fasted and refed mice through its effects on PEPCK mRNA stability. The effects of the inhibitors on PEPCK mRNA levels indicate the inhibitors were efficacious in these studies.

Example 11

Pancreatic Hormones and Glucose

The physiological hallmarks of the fasting-feeding transition are increased circulating insulin and decreased circulating glucagon. In the studies shown in FIG. 6, fasted and refed sham-injected mice had serum glucose concentrations of 84.4±5.1 and 1.21±8.0 mg/dl, serum insulin concentrations of 0.491±0.203 and 1.3±0.256 pmol/ml, and serum glucagon concentrations of 143±22.4 and 81.4±13.2 pg/ml, respectively.

To investigate whether these hormones an: involved in the postprandial induction of GRP78 mRNA, the effects of cAMP, glucagon, and STZ-induced diabetes on the response were examined. Administration of either dibutyryl cAMP or glucagon reduced the response of GRP78 mRNA to feeding (FIG. 6A). Vehicle alone had no effect. Likewise, STZ-induced diabetes resulted in a blunted response to feeding although it did not modify the fasting level of GRP78 mRNA. When STZ-induced diabetes was combined with cAMP administration, the postprandial induction of GRP78 mRNA was obliterated. The mRNA remained at fasting levels Without being bound to any particular mechanism, these results suggest that glucagon, acting to increase intracellular cAMP levels, suppresses chaperone gene transcription, or possibly GRP78 pre-RNA stability. Further, they suggest that insulin is required for full responsiveness of the chaperone genes to decreased intracellular cAMP.

Example 12

Luminal Filling

Luminal filling can lead to the release of some gastrointestinal polypeptide. For this reason, we investigated the role of luminal stimuli on the chaperone mRNA response. Fasted mice were refed a nonnutritive paste of cellulose (a normal component of their regular diet) and mineral oil. The mice initially consumed the mixture enthusiastically. Stomach filling was confirmed for each mouse by postmortem examination. Cellulose-mineral oil consumption produced a minor but significant increase in GRP78 mRNA (FIG. 6B), without producing a change in plasma glucose, insulin, or glucagon concentrations.

Example 13

Adrenal Hormones

To investigate the role of adrenal hormones in the postprandial induction of GRP78 mRNA, we examined the effects of feeding in adrenalectomized mice (FIG. 7). Neither adrenalectomy nor sham surgery had any effect on the fasting levels of GRP78 mRNA. However, adrenalectomy increased the magnitude of the postprandial induction of the mRNA by approximately 2-fold over that found is refed, sham-operated mice. The feeding response of GRP94, ERp72, and GRP170 were also enhanced in the adrenalectomized mice (data not shown). Thus, the increase is a generalized ER chaperone response. Administration of dexamethasone to adrenalectomized mice increased the basal level of GRP78 mRNA during starvation, although not significantly (FIG. 7). However, dexamethasone administration had no effect on the feeding induction of the gene, suggesting its absence from adrenalectomized mice is not responsible for the enhancement of the feeding response.

Example 14

Preparation of Test Groups for Short-term CR Studies

Three groups of 30 month old mice were utilized for these studies. Male B6 $C3F_1$ mice were maintained as described (Dhahbi et al. (1998) J. Gerontol 53A: B180). Mice were weaned at 28 days and housed individually. The composition of the defined diets used have been described. They are formulated so that only the amount of carbohydrate consumed varied between the CR and control mice. A group of control mice was fed a purified, semi-defined diet from 6 weeks of age. Control mice consumed approximately 105 kcal per week from weaning. This is approximately 10% less than the amount of food thought to support optimal growth, fertility and fecundity in mice {Subcommittee on Laboratory Animal Nutrition & Committee on Animal Nutrition 1978 ID: 5480}. Subjectively, these mice appeared neither fat or lean. A group of calorically restricted mice (CR mice) were fed a diet reduced in dietary carbohydrate such that the mice consumed approximately 40% fewer calories than control mice. The long term CR mice consumed approximately 55 kcal per week from weaning. The short term CR mice were fed 105 kcal until the age of 29 months. They were then fed 80 kcal of control diet for 2 weeks, followed by 55 kcal of CR diet for two weeks. The mice were fed daily at 0900 hours. They had free access to water. For the studies, mice were fed a normal allotment of food Monday morning, and all the food was eaten within 45 minutes. They were fasted for 24 hours, and killed on Tuesday morning. At the time of use, the long term CR, short term CR and control mice weighed 22.8±1.4, 25.22±0.3 and 37.2±2.4 g, respectively. The mice were approximately 30 months old when killed.

Mice were killed by cervical dislocation and the liver rapidly removed and flash frozen in liquid nitrogen. Approximately 0.2 g of frozen liver was homogenized for 40 s in 4 ml of TRI Reagent (Molecular Research Center, Inc., Cincinnati, Ohio) using a Tekinar Tissuemizer (Tekmar Co., Cincinnati, Ohio) at a setting of 55. RNA was isolated as described by the supplier.

[GeneChip o] *O*ligonucleotide-based high-density array RNA expression assays were performed according to the standard Affrymetrix protocol. The biotinylated, fragmented cRNA was hybridized to the Mu11KsubA and Mu11KsubB[GeneChip] *GeneChip*® arrays (Affymetrix, Santa Clara, Calif.), which contain targets for more than 11,000 known mouse genes and ESTs. The arrays were washed, stained and scanned. Scanned image analysis and data quantification were performed using the Affymetrix [GeneChip] *GeneChip*® analysis suite v3.2 at default parameter settings. Resultant data were normalized by global scaling.

Data analysis. Data sets were normalized furher using GeneSpring 3.0 (Silicon Genetics, San Carlos, Calif.). Negative expression levels were forced to zero, and the expression data for each animal divided by the median of all experimental values for that chip above an expression level of 10. This step reduced cliip-to-chip signal variation. Fold change in expression was calculated by dividing the mean of the expression levels in the CR groups by the mean of the expression levels in the control group.

Statistical analysis. To test for significance of the effect of diet on gene expression, one-way ANOVA was followed by Fisher's test ($P<0.05$). Genes were placed in expression pattern groups (Table 2) for which they passed both tests. All statistical analyses were performed using Minitab Statistical Software.

Example 15

Gene Expression in Long and Short Term CR Mice

The global patterns of hepatic gene expression in the three groups of mice as displayed by GeneSpring 3.0, are shown in FIG. 8. The 11,000 genes assayed in the study are grouped according to both structure and function by the GeneSpring gene clustering algorithm across the horizontal axes of the figure. While this representation of the data cannot be subjected to statistical tests, subjective examination of this color coded representation of the data obtained immediately suggests that striking similarities exist in the gene expression profile of long and short term CR mice. Likewise, examination of the figure suggests that both CR expression profiles are very different than the profile of control mice. An average-linkage hierarchical clustering dendrogram calculated from the data by the GeneSpring clustering algorithm is shown to the left of the expression profiles. The dendrogram shows that the algorithm clustered the short- and long-term CR groups together, separated from the control group. This analysis agrees with our subjective interpretation of the expression profile.

Another aspect of this representation of the data was of interest. Significantly larger areas of blue were found in the expression profile of the control mice. These areas represent genes for which expression was not detectable. In both groups of CR mice, many of these regions were red, indicating higher levels of expression. Thus, a major effect of CR was the activation of specific gene expression.

To quantify the similarities in gene expression among groups of mice, a global expression correlation coefficient was calculated for each possible pair of mice. Table 1 shows the nine by nine matrix of these pairwise comparisons. The values are a measure of the similarities in gene expression between pairs of mice. Because the mice were genetically identical, the intra-group values provide a measure of the maximum correlations attainable. The inter-group correlations of the short- and long-term CR mice were similar to their intra-group correlations, indicating that gene expression in all CR mice was similar. In contrast, the control mice have little correlation with the mice in either CR group. This analysis suggests that short- and long-term CR had highly similar effects on overall patterns of specific gene expression.

TABLE 1

Pairwise comparisons of the global gene expression correlation coefficient calculated for each possible pair of mice.

| | CR | | | CONTROL | | | SWITCHED | | |
|---|---|---|---|---|---|---|---|---|---|
| CR | 1.00* | 0.25 | 0.32 | 0.01 | 0.04 | −0.04 | 0.16 | 0.17 | 0.18 |
| | | 1.0 | 0.27 | −0.03 | 0.03 | −0.01 | 0.13 | 0.12 | 0.18 |
| | | 1.00 | | 0.02 | 0.02 | −0.02 | 0.18 | 0.14 | 0.21 |
| CONTROL | | | | 1.00 | 0.29 | 0.42 | 0.0 | 0.03 | 0.07 |
| | | | | | 1.00 | 0.28 | 0.07 | 0.10 | 0.01 |
| | | | | | | 1.00 | −0.02 | 0.02 | 0.05 |
| SWITCHED | | | | | | | 1.00 | 0.24 | 0.18 |
| | | | | | | | | 1.0 | 0.16 |
| | | | | | | | | | 1.00 |

Example 16

Long- and Short-term CR Induced Expression of the Same Genes

The pseudogene function of GeneSpring 3.0, and statistical analysis of the data were utilized to sort the genes into one of seven possible categories of relative gene expression. These groups were: expression not different among groups; expression high in long-term CR, low in control, and high in short-term CR (termed, high-low-high) (Appendix A); expression low in long-term CR, high in control, and low in short-term CR (low-high-low) (Appendix B); expression low in long-term CR and control, but high in short-term CR (low-low-high) (Appendix C); expression high in long-term CR and control, and low in short-term CR (high-high-low) (Appendix D); expression high in long-term CR, and low in control and short-term CR (high-low-low) (Appendix E); and expression low in long-term CR and high in control and short-term CR (low-high-high) (Appendix F). The vast majority of the genes were not different among groups, and will not be discussed further.

Table 2 shows the number of genes and expressed sequence tags (ESTs) in each of the other groups. Ninety percent or these genes and ESTs were in the high-low-high and low-high-low groups. In these groups, the short- and long-term CR expression patterns are most similar. The other 4 groups accounted for only 10% of the remaining genes ans ESTs. These data indicate that short- and long-term CR produced remarkably similar effects on the expression of more than 11,000 hepatic genes and ESTs. A complete listing of the expression data for the genes and ESTs in each group is available [(http://wwwbiochemistry.ucr.edu/faculty/spindler.html/GeneChipData) (This URL will be activated upon allowance of this application)] *on the internet*.

By far the most common response to short- and long-term CR was the high-low-high expression pattern. It accounted for nearly 86% of the genes and ESTs in the groups. Thus, the most common effect of short- and long-term CR was the activation of gene expression. To determine whether short- and long-term CR induced expression to the same degree in the high-low-high group, we tabulated the number of known genes for which expression was statistically the same in the two groups. In high-low-high, 303 of 340 known genes (89%) were expressed at the same level in the short- and long-term CR groups. For 26 of these genes (8%), expression in the long-term CR mice was statistically greater. For 11 genes (3%), expression was greater in the short-term CR group. Thus, short- and long-term CR induced the expression of the vast majority of these genes to the same levels.

Of the genes in the high-low-high group, 146 of 340 genes were activated from undetectable levels in the control mice to much higher, but very similar levels in both CR groups. Expression of these genes averaged 1.25±0.25 and 1.23±0.23, in the short- and long-term CR groups, respectively. These observations reinforce the idea that short- and long-term CR have highly homologous effects on the expression of genes.

To further understand the genomnic effects of CR, we identified the genes in the high-low-high group described above.

TABLE 2

| GENES WHICH DIFFER FROM CONTROL IN RESPONSE TO CR | | | | | |
|---|---|---|---|---|---|
| LT CR* | CONTROL | ST CR** | GENES | ESTs | PERCENT |
| High | Low | High | 340 | 860 | 85.7 |
| Low | High | Low | 23 | 37 | 4.3 |
| High | High | Low | 4 | 9 | 0.9 |

TABLE 2-continued

| GENES WHICH DIFFER FROM CONTROL IN RESPONSE TO CR | | | | | |
|---|---|---|---|---|---|
| LT CR* | CONTROL | ST CR** | GENES | ESTs | PERCENT |
| Low | Low | High | 13 | 19 | 2.3 |
| High | Low | Low | 26 | 55 | 5.8 |
| Low | High | High | 9 | 6 | 1.1 |

*Long-term CR
**Short-term CR

Example 17

Immune System Activation: The Immune Theory of Aging

Many of the genes which were induced by CR in the long and short term CR group were genes involved with immune system activation. Without being limited to any specific mechanism, this result provides support for the theory that the immune system plays a central role in the rate and many of the pathologies of aging. Slightly more than 130 T-cell receptor, IgG, IgA, IgD, IgK, and IgM, genes were present in the high-low-high group. The average fold relative expression of these mRNAs in the long and short term CR groups was 1.24±0.86 and 1.23±0.25, verses 0.16±0.16 in the control group. Thus, CR increased immunoglobulin and T-cell receptor expression more then 10-fold. It is highly unlikely that this increase was due to an increase in the amount of blood in the CR livers. The level of globin mRNA found in these mRNA samples was actually reduced by about 20% in the long and short term CR groups. No statistically significant difference was found in the globin mRNA concentration in the blood of these animals.

Other changes in gene expression indicate that CR activates the immune system (Table 3). As can be seen in the table, both long and short term CR induced the expression of hemopoietic and lymphopoetic cytokines, hormones, signal transduction proteins, protein kinase modulators of the cell cycle and signal transduction, cell-surface receptors, and transcription factors. Not shown are a group of 20 immune cell specific genes known to be involved in endocytosis, cell adhesion, phagocytosis, potassium channels, lymphocyte activation, VDJ recombination, and immune cell activation which were strongly and significantly induced by CR (3- to 40-fold; P≦0.037). Together, these data evidence that CR enhances the activity of the immune system.

TABLE 3

| Immune system genes activated by short- and long-term CR | | | |
|---|---|---|---|
| LTCR* | STCR* | P | GENE |
| | | | Hormones/Cytokines/Chemokines |
| 4 | 4 | 0.003 | Antigen, B cell receptor, L43567 |
| 53 | 55 | <0.001 | Calcium/calmodulin-dependent protein kinase IV (Camk4); multifunctional serine-threonine protein kinase; T cells; X58995 |
| >100 | >100 | <0.001 | Chemokine (C—C) receptor 1 (Cmkbr1); growth inhibitory effects; liver and spleen; U28404 |
| 13 | 17 | <0.001 | Chemokine (C—C) receptor 5 (Cmkbr5); induces mobilization of intercellular calcium; beta-chemokine; leucocyte cheatoallractant; liver, thymus, spleen, elsewhere: LT62976 |
| >100 | >100 | 0.003 | Chemokine (C-X-C) receptor 4 (Cmkbr4); integral membrane G-protein-coupled receptor; chemotaxis and calcium flux; directs monocytes and lymphocytes to their target tissues; thymus, T cells, and monocytes; ET62920 |

TABLE 3-continued

Immune system genes activated by short- and long-term CR

| LTCR* | STCR* | P | GENE |
|---|---|---|---|
| 19 | 21 | 0.002 | Colo9ny stimulating factor 1 (macrophage) (Caf1); receptor; liver; X06368 |
| 10 | 8 | 0.016 | Complement receptor 2 (Cr2); Late pre-B cells; M35684 |
| 3 | 2 | 0.015 | Interferon beta type 1; growth factor; T helper cell differentiation factor; antiviral; modulated immune response to foreign and self-antigenes; immune system cells, others; V00755 |
| 11 | 10 | <0.001 | Interferon-related developmental regulator (Ifrd1); T cells; V00756 |
| 9 | 6 | 0.044 | Interleukin 2 (Il2); stimulated proliferation of activated T lymphocytes; M16762 |
| >100 | >100 | 0.015 | Interleukin 2 receptor (Il2r); T cells; M26271 |
| 2 | 2 | 0.014 | Interleukin 6 (Il6); promoter B cell maturation to tg-secreting cells; activation of T cells; some helper T cells and macrophages; X54542 |
| 5 | 6 | 0.004 | Interleukin 7 (Il7); growth factor, B cell progenitors; X07962 |
| 4 | 3 | 0.046 | Killer cell lectin-like receptor, subfamily A, member 3 (Klra3); Ly-49C; involved in graft rejections; subpopulation of natural killer cell; U49866 |
| >100 | >100 | 0.034 | Killer cell lectin-like receptor, subfamily A, member 6 (Klra6); Ly-49F; NK cell surface antigen; determinant of IL-2-activated NK cell proteins; NK cells, U10092 |
| 13 | 11 | <0.001 | Lymphocyte antigen 84 (Ly84); signal transduction protein 2; T cells; D13695 |
| 5 | 6 | 0.007 | Mast cell protease 7 (Mcpt7); released when mast cells are activated; mast cells; ET61471 |
| 3 | 2 | 0.037 | Myc box dependent interacting protein 1 (Bin1); endocytosis and signal transduction; recycling synaptic vesicle components; macrophages, neurons, endocrine cells; U86405 |
| >100 | >100 | <0.001 | Paired-Ig-like receptor A1 (Pira1); activates B lymphocytes, dendritic and mycloid-linage cells; ET62839 |
| 5 | 4 | 0.027 | Paired-Ig-like-receptor A6 (Pira6); appears to activate immunoglobulin-related receptor; H lymphocytes, myeloid lineage cells; ET62844 |
| 3 | 4 | 0.038 | Preprosomatostatia (Stnst); regulates T cell IFN-gamma production; macrophages, nervous system; X51468 |
| >100 | >100 | <0.001 | Protein tyrosine phosphatase, receptor type B (Ptpre); transmembranal, receptor-like form and a cytoplasmic, non-receptor form; hematopoietic tissues; ET61424 |
| 23 | 41 | 0.010 | Proviral integration site (Pim2); serine/threonine kinase 2; cell proliferation; mitogen stimulated; long-term potentiation in hippocampus; immune and epithelial cells, CNS; L41495 |
| | | | Receptors/Signal Transduction Proteins |
| 11 | 8 | 0.001 | Small inducible cytokine subfamily, member 2 (Scyb2); small inducible cytokine; macrophages; X5379H |
| 8 | 8 | 0.002 | Son of sevenless 1, homologue 1 (*Drosophila*) (Sos1); Ras-specific exchange factor; T cells; Z11574 |
| >100 | >100 | <0.001 | Son of sevenless 2 homologue 2 (*Drosophila*) (Sos2); Ras-specific exchange factor; T cells; Z11664 |
| >100 | >100 | 0.002 | Spleen protein kinase (Syk); signal transduction; lymphopoietic and haematopoietic cells, plateleta, anacrophages and neutrophils; ET61263 |
| >100 | >100 | 0.048 | Tbel; domains homologous to tre-2 oncogene and yeast mitosis regulators BUB2 and cdc16; nuclear localization; B lymphocytes; deadritic cells, myeloid-linage cells; U33005 |
| 2 | 2 | 0.044 | Thrombin receptor; transmembrane G-protein-coupled receptor; activated by serine protease cleavage; mitogen and apoptosis inducer following vessel injury; plateleta, monocytes, endothelial cells, neuronal and glial cells; U36757 |
| >100 | >100 | 0.002 | Weel homologue (*S. pombe*) (Weel); inhibits entry into mitosis by phosphorylatios of the Cdc2 kinase; lymphocytes; D30743 |
| | | | Transcription Factors |
| 38 | 35 | <0.001 | Abelson nurine leukemia oncogene (Abl); nonreceptor tyrosine kinase; role in cell progression, cell proliferation and differentiation; liver, B cells, others; X07540 |
| >100 | >100 | 0.047 | Homeo box A4 (Hoxa4); transcription factor; embryonic spinal cord and adult testis; X13538 |
| 4 | 7 | 0.026 | Homeo box B4 (Hoxb4); transcription factor; embryonic development; haematopoiesis; NK cells; M36654 |
| 6 | 10 | 0.029 | Homeo box B7 (Hoxb7); transcription factor; embryonic development; haematopoiesis; developing embryo; blood, bone marrow, natural killer cells; X06762 |
| 8 | 9 | <0.001 | Homeo box C6 (Hoxc6); transcription factor; embryogenesis; haematopoiesis; lliver and many other tissues; X16510 |
| 40 | 36 | 0.001 | Homeo box D1 (Hoxd1); transcription factor; neurogenesis; developing CNS and forelimb bud; X60034 |

TABLE 3-continued

| Immune system genes activated by short- and long-term CR | | | |
|---|---|---|---|
| LTCR* | STCR* | P | GENE |
| >100 | >100 | <0.001 | Nuclear factor of activated T cells, cytoplasmic 2 (Nfatc2); T cell transcription factor isoform B; T cells; U36575 |
| 5 | 5 | 0.001 | SRY-box containing gene 4 (Sox4); Sox gene family transcription factor; thymus, bone marrow, gonads; ET62444 |
| 2 | 2 | 0.012 | Zinc finger protein 79 (Zfp79); Kruppel type zinc finger putative transcriptional repressor; associates with RB in vitro; haematopoietic cells, perhaps others; U29513 |
| | | | Primary Response Genes |
| >100 | >100 | 0.005 | Fos-like antigen-1 (Fosl1); spleenocytes; U34245 |
| >100 | >100 | <0.001 | Immunity associated protein, 38 kDa (Imap38); spleenocytes; Y08026 |
| >100 | >100 | <0.001 | Immunorespossive gene 1 (Irg1); activated by bacterial LPS treatment; macrophages; L38281 |
| >100 | >100 | <0.001 | Prostaglandin-endoperoxide synthase (Ptgs2); putative mediator of inflammation; induced by growth factors and cytokines; monocytes and fibroblasts; M88242 |
| 388 | 353 | 0.001 | T-cell actue lymphocytic leukemia 2 (Ts12); putative basic helix-loop-helix transcription factor activated in T-cell acute lymphoblastic leukemia; T cells; M81077 |
| >100 | >100 | <0.001 | Tumor necrosis factor inducted protein 3 (Tnfip3); putative helix-loop-helix transcription factor activated in T-cell acute lymphoblastic leukemia; lymphocytes; U19463 |
| | | | Cell Adhesion/Membrane Components |
| >100 | >100 | 0.002 | ADP-ribosyltransferase 2s (Art2s); homologue of the rat T cell differentiation marker RT6; cell-cell signaling; cytotoxic T lymphocytes; X52991 |
| 9 | 9 | 0.013 | Cadherin 9 (Cdh9); calcium-binding membrane glycoprotein; cell adhesion molecule; thymocytes; U69136 |
| 6 | 5 | 0.015 | CD22 antigen (Cd22); mediated B cell interactions with endothelial cells; B cells; L16928 |
| 7 | 7 | 0.002 | CD53 antigen (Cd53); pan-leukocyte antigen; cell membrane glycoprotein; thymocytes; X97227 |
| 40 | 36 | <0.001 | Erythrocyte protein bond 7.2 (Epb7.2); involved in Na+/K+ permeability of cells; spleen, lung, testis; X91043 |
| 8 | 8 | 0.006 | Integria alpha 4 (Iiga4); cell adhesion; lymphocytes; X53176 |
| >100 | >100 | <0.001 | Mannose receptor, C type 2 (Mrc2); cell adhesion; antigen presentation; widespread tissue distribution, fetal liver, U56734 |
| | | | Immune Cell Function |
| 38 | 44 | <0.001 | Cytochrome b-245, beta polypeptide (Cybb); gp91phox; flavocytochrome mediating electron transfer from NADPH to molecular oxygen in the respiratory burst oxidase; phagocytes; U43384 |
| 8 | 8 | <0.001 | Cytotoxic T lymphocyte-associated protein 2 beta (Ctla2b); homologue of cysteine protease proregion, T cells; X15592 |
| >100 | >100 | <0.001 | GraezyineG (Gzng); CTL serine protease 3; may play a role in cytolytic lymphocyte activation; T lymphocytes; X14092 |
| >100 | >100 | 0.007 | Helicase, lymphoid specific (Hells); replication, repair, recombination and transcription; T and B cells; U25691 |
| >100 | >100 | 0.001 | Mast cell protease 4 (Mcpt4); secretory granule serine protease; peritoneal and most connective tissue mast cells; M55617 |
| 5 | 6 | 0.007 | Mast cell protease 7 (Mcpt7); released when mast cells are activated; mast cells; ET61471 |
| 8 | 8 | 0.005 | Potassium voltage gated channel, shaker related subfamily, member 2 (Kena2); T cells, myelinating Schwann cells; M30440 |
| 3 | 3 | 0.003 | Terminal deoxynucleotidyl transferase (Tdt); VDJ assembly; recombination; earliest stage B and T cells; X04123 |

*Fold of control

Further support for this view was found in the liver specific genes which were strongly induced in expression by CR (Table 4). Long and short-term CR significantly enhanced the expression of the CD44 hyaluronan receptor gene, which has a role in lymphocyte homing and activation. Likewise, CR activated the mRNA abundance of the chemokine receptor 4, which is also involved in stimulating growth of pre-B cells; the mannose receptor, C type 2, which is involved in antigen presentation; colony stimulating factor 1, which is a macrophage growth factor; and proteaseome 3, which enhances the generation of class I binding peptides.

TABLE 4

| LTCR* | STCR* | P | GENE |
|---|---|---|---|
| | | | Liver specific and ubiquitous genes |
| | | | Cytokines/Growth Factors |
| 12 | 7 | 0.003 | C-Fow induced growth factor (Fief); secreted growth factor; mitogenic and morphogenic activity; endothelial cells of liver during embryonic development; X99572 |
| 2 | 2 | 0.002 | Fibroblast growth factor 2 (Fgf2); mitogen, differentiation and survival factor, angiogenic factor; stimulates hepatocyte |
| >100 | >100 | 0.001 | Fibroblast growth factor 3 (Ffg3); liver epithelial cells; Y00648 |
| 3 | 3 | 0.012 | Fibroblast growth factor 7 (Ffg7); liver epithelial cells; ET62118 |
| >100 | >100 | 0.001 | Follistatis (Fst); binds and inactivates activia; control of the inflammatory cascase; liver; Z29532 |
| >100 | >100 | 0.005 | Inhibin beta B (Iabbb); transforming growth factor beta (TGF-beta) superfamily member; liver and elsewhere; X69620 |
| >100 | >100 | 0.001 | Inhibin beta E (Iabbe); transforming growth factor beta (TGF-beta) superfamily member; liver and elsewhere; U96386 |
| 13 | 9 | 0.000 | Interferon alpha gene family leukocyte (Iafa); inhibition of cell proliferation; ubiquitous; M28587 |
| 3 | 2 | 0.015 | Interferon beta type 1; growth factor; T helper cell differentiation factor; antiviral; modulates immune responses to foreign and self-antigens; ubiquitous; V00755 |
| 11 | 11 | 0.001 | Interferon-beta (Ifnb); inhibitor of inflammations; liver and other cells; J00424 |
| 13 | 13 | <0.001 | Neurotrophin 3 (Ntf3); secreted protein; binds high affinity receptor trk C; may be involved in postestial development; liver parenchymal cells, cerebellu, thymus, other; X53257 |
| 4 | 5 | 0.003 | Preproendothelin 1 (Edn1); activates p38 MAP kinase and JNK; portal vein contriction; hepatic stellate cells, liver and arterial smooth muscle cells, others; U07982 |
| 10 | 15 | 0.003 | Transforming growth factor beta 2 (Tgfb2); cell proliferation; liver stellate cells; X57413 |
| | | | Cell Surface Receptors |
| >100 | >100 | 0.020 | Bradykinin receptor beta (Bdkrb); G-protein-coupled membrane bouad; T-kininogen modulation during acute phase protein synthesis; liver (ubiquitous); ET61559 |
| 2 | 2 | 0.017 | CD44 antigen (Cd44); receptor for hyaluronan; cell surface glycoprotein; hyaluronan clearance from the blood; lymphocyte homing and activation; liver, CNS, other; U57612 |
| >100 | >100 | <0.001 | Chemokine (C—C) receptor 1 (Cmkbr1); mediates growth inhibitory effects of the chemokine; liver and spleen; U28404 |
| 12 | 8 | 0.013 | Chemokine (C-X-C) receptor 4 (Cmkar4); primary receptor stromal cell-derived factor/pre-B growth stimulating factor; seven transmembrane domain receptor; liver and bone marrow; X99581 |
| >100 | >100 | <0.001 | Fibroblast growth factor receptor 2 (Fgfr2); membrane;spanning tyrosine kinase; activated by three members of the FGF family; liver development; liver parenchymal cells and others; M86441 |
| 4 | 3 | 0.001 | Leptin receptor (Lepr); transmembrane receptor; liver, lung, muscle, brain, other; ET61693 |
| 4 | 3 | 0.027 | Melanocortin 5 receptor (Mc5r); G-protein-coupled receptor, stimulates adenylyl cyclase; widely expressed; X76295 |
| 3 | 4 | 0.029 | Pancreatic polypeptide receptor 1 (Ppyr1); aeuropeptide Y; peptide YY receptor; O-protein-coupled; liver; U40189 |
| >100 | >100 | <0.001 | Proteaseome 3 (Psme3); Ki antigen; cell proliferation; enchances generation of class I binding peptides; liver, broad tissue distribution; U60330 |
| >100 | >100 | <0.001 | Purinergic receptor P2X, ligand-gated ion channel 1 (P2rx1); mediated Ca(2+) influx; liver, ubiquitous; X84896 |
| 64 | 68 | 0.001 | Ryasodine receptor 2 (Ryr2); endoplasmic reticulon membrane Ca2+ channels; controls cytosolic calcium levels; liver, cardiac muscle, neurons, most excitable cells; X83933 |
| >100 | >100 | 0.003 | Transferrin receptor (Trfr); cell surface glycoprotein; cell growth; iron uptake; liver; X57349 |
| | | | Signal Transduction/Cell Cycle/Cell Growth |
| 38 | 35 | <0.001 | Abelson murine leukemia oncogene (Abl); nonreceptor tyrosine kinase; role in cell proliferation and differentiation; liver, B cells; X07540 |
| >100 | >100 | 0.006 | Cyclin-dependent kinase inhibitor 1B (P27) (Cdkn1b); cell cycle; ubiquitous; U10440 |
| 35 | 40 | 0.003 | Gusnine nucleotide binding protein, alpha inhibiting 1 (Gnail); liver, cerebral cortex, others; U38501 |
| >100 | >100 | 0.013 | Gusnine nucleotide binding protein beta 4 (Gab4); liver, brain, blood cell; M63658 |
| >100 | >100 | 0.001 | Histamine recepotr H1 (Hrb1); coupled to phosphoinositide turnover-calcium mobilization signaling pathway; regulates IOF-1 |

TABLE 4-continued

| LTCR* | STCR* | P | GENE |
|---|---|---|---|
| | | | Liver specific and ubiquitous genes |
| | | | expression and cell proliferation; regulates thyroxine transport into hepatocytes; liver, brain, spleen (ubiquitous); D50095 |
| >100 | >100 | 0.002 | Interferon-activated gene 204 (Ifi204); mediates antimicrobial, immunomodulary and cell growth-regulatory activities of interferons; nucleoli; M31419 |
| 4 | 4 | 0.004 | Kinase interacting with leukemia-associated gene (Kis); cytosolic phosphoprotein; integration of intracellular proliferation and differentiation signaling; ubiquitous; X82320 |
| 9 | 8 | 0.004 | MAD homologue 5 (Madh5); downstream component in the TGF-beta family signaling cascase; liver development angiogenesis; liver; ET62570 |
| >100 | >100 | 0.002 | MAP kinase kinase kinase (Map3k1), serine-threonine kinase; regulates sequential protein phosphorylation pathways involving mitogen-activated protein kinase (MAPKs); ubiquitous; ET61257 |
| >100 | >100 | 0.002 | Mitogen activated protein kinase 1 (Mapk1); signal transduction; cell proliferation, differentiation, and apopiosis; liver, ubiquitous; U85608 |
| >100 | >100 | 0.004 | NIMA-related expressed kinase (Nek1); ubiquitous; S45828 |
| 3 | 3 | 0.041 | Neuroblastoma ras oncogene (Nras); key component of growth signaling pathways; liver, wide tissue distribution; X13664 |
| >100 | >100 | <0.001 | Phosphatidylinositol 3-kinase regulatory subunit, polypeptide 1 (p85alpha) (Pik3r1); role in cell growth, differentiation, survival, and vesicular transport; liver; ET61628 |
| >100 | >100 | 0.003 | Phospholipase C, gamma 1 (Pleg1); produces second messengers of signal transduction pathways related to cell proliferation; ubiquitous; ET63005 |
| >100 | >100 | <0.001 | Proteasome 3 (Psme3); Ki antigen; cell proliferation; enchances the generation of class I binding peptides by altering the cleavage pattern of the proteosome; liver, neurons, broad tissue distribution; U60330 |
| 3 | 2 | 0.002 | Protein tyrosine phosphatase, non-receptor type 16 (Ptpn16); growth factor-induced immediate early gene; dephosphorylates MAP kinase; liver parenchyenal and vascular smooth muscle cells, others; X61940 |
| 11 | 12 | 0.001 | Ras-GTPase-activating protein SH3-domain binding protein 2 (G3bp2-pending); essential for Ras signaling; ubiquitous; U65313 |
| 2 | 2 | 0.001 | Rhodopsin kinase (Rhok); small GTPase and serine/threonine protein kinase; regulates actia cytoskeletal reorganization; enhances secretion; ubiquitous except for brain and muscle; U58513 |
| 15 | 14 | 0.016 | Ros 1 proto-oncogene (Ros1); embryonic develoopment; tyrosine kinase catalytic domains; expressed in neoplastic and fetal tissues; neoplastic and fetal tissues; U15443 |
| 6 | 4 | 0.010 | SUMO-1 activating enzyme subunit 1; conjugates SUMO-1 (a small ubiquitin-like protein) to other proteins; modification of I Kappy B alpha blocks NF kappa B-dependent transcriptional activation; ubiquitous; AA162130 |
| >100 | >100 | <0.001 | Wingless related MMTV integration site 10b (Wat10b); development regulation of cell growth and differentiation; ET62229 |
| | | | Nuclear Receptors |
| 19 | 17 | 0.016 | Thyroid hormone receptor alpha (Thra); energy balance, thermoregulation, substrate uptake; liver; X07751 |
| 10 | 9 | 0.003 | Glucocorticoid receptor 1 (Gd1); energy balance; substrate uptake; liver; X04435 |
| 45 | 42 | <0.001 | Nuclear receptor subfamily 2, group P member 1 (Nr2f1); COUP-TF1; orphan steroid hormone receptor, transcription factor; liver, X74134 |
| >100 | >100 | 0.010 | Nuclear receptor subfamily 2, group F member 2 (Nr2(2); apolipoprotein regulatory protein 1; member of the COUP-family of steroid hormone orphan reception; liver, lung, kidney; X76653 |
| | | | Transcription Factors |
| 4 | 3 | 0.016 | Sine oculis-related homeobox 1 homologue (*Drosophila*) (Six1); AREC3; expressed in many cell-types during development; ET61028 |
| 9 | 7 | 0.003 | cAMP responsive element binding protein 1 (Creb1); a mediator of cAMP responsive transcriptional regulation; ubiquitous; X67719 |
| >100 | >100 | <0.001 | Reticuloendotheliosis (Rel); c-rel; member of the ReVauclear factor (NF)-kappa B family of transcriptional factors; ubiquitous; X15842 |

TABLE 4-continued

| LTCR* | STCR* | P | GENE |
|---|---|---|---|
| | | | Liver specific and ubiquitous genes |
| >100 | >100 | <0.001 | E4F transcription factor 1 (E4f1); DNA binding transcription factor; ubiquitous; X76858 |
| 4 | 4 | 0.026 | Forkhead box C2 (Foxc2); transcription factor; hepatocytes; X74040 |
| 11 | 11 | 0.001 | Homeo box A9 (Hoxa9); transcription factor; embryogenesis; M28449 |
| >100 | >100 | 0.003 | Homeo box msh-like 1 (Max1); transcription factor; early stage of eye developmental regulation in embryo; embryogenesis; X59251 |
| 2 | 3 | 0.003 | Inhibitor of DNA binding 4 (Idb4); domineer negative regulator of bHLH transcription factors; myogenesis, neurogenesis D83 and haematopoiesis; liver and elsewhere; X75018 |
| >100 | >100 | 0.010 | Myogen factor 5 (Myf5); transcription factor, embryonic liver and heart; X56182 |
| 6 | 8 | 0.003 | Nuclear transcription factor-Y alpha (Nfye); CAAT-box DNA binding protein subunit A; involved in activation of many hepatic genes; ubiquitous; X55315 |
| 3 | 3 | 0.018 | Paired box gene 2 (Pax2); Pax2 transcription factor; developing embryo excretory and CNS; X55781 |
| 12 | 13 | 0.003 | RE2-silencing transcription factor (Rest); transcription factor; represses expression of neuronal genes; many noancuronal cells and tissues; U13878 |
| >100 | >100 | 0.002 | Sine oculia-related homeobox 1 homolog (*Drosophila*) (Six1); homeobox; development of limb teadons; skeletal and smooth muscle cells; X80339 |
| >100 | >100 | 0.005 | SRY-box containing gene 12 (Sox12); transcription factor; Sox family plays important role in development; developing embryos; ET62446 |
| 2 | 3 | 0.032 | T-box 4 (Tbx4); DNA binding domain putative transcription factor; putative roll in inductive interactions during embryogenesis; embryonic development; ET62078 |
| >100 | >100 | 0.009 | Trans-acting transcription factor 1 (Sp1); transcription factor; component of some hepatic glucose response elements, ubiquitous; X60136 |
| >100 | >100 | 0.024 | Transcription elongation factor A 1 (Tcea1); transcription elongation factor; liver; D00925 |
| 14 | 12 | <0.001 | Yes-associated protein, 65 kDa (Yap); transcription activator, ubiquitous; X80508 |
| 10 | 10 | <0.001 | Zinc finger protein 37 (Zfp37); putative transcription factor; peroxisome proliferator responsive; liver; X89264 |
| >100 | >100 | 0.009 | Zinc finger protein 61 (Zfp61); putative transcription factor, liver, elsewhere; L28167 |
| | | | Translation/Splicing/Rna Processing Factors |
| 7 | 7 | 0.001 | Cytoplasmic polyadenylatice element binding protein (Cpeb); RNA binding protein that promotes polyadenylation and translational activation; ubiquitous; Y08260 |
| 4 | 4 | 0.011 | Eukayotic translation initiation factor 1A (Eif1a); ubiquitous; U28419 |
| >100 | >100 | <0.001 | Ribosomal protein L32, pseudogene (Rp132ps); ubiquitous; X02060 |
| >100 | >100 | 0.000 | Ribosomal protein L7 (Rp17); incorporated into 60 S subunit; ubiquitous; X57960 |
| 18 | 13 | 0.001 | Signal recognition particle 9 kDa (Srp9); synthesis and translocation of membrane and secreted proteins into the endoplasmic reticulum; ubiquitous; X78304 |
| >100 | >100 | 0.004 | Splicing factor arginine/serine-rich 3 (Sfrs3); splicing factor belonging to the highly conserved family of SR proteins; regulation of constitutive and alternative splicing; ubiquitous; X91656 |
| | | | Chromatin Structure |
| 4 | 5 | 0.009 | Chromobox homologue (*Drosophila* HP1beta) (Cbx); modifs chromatin heritably activating or silencing genes; ubiquitous during development; X56690 |
| >100 | >100 | 0.026 | Histone H1 subtype e (Hle); chromatin structure; ubiquitous; L04141 |
| >100 | >100 | <0.001 | Histone H1; chromatin structure; ubiquitous; J03482 |
| 109 | 70 | <0.001 | Histone H1b; chromatin structure; ubiquitous; ET62262 |
| >100 | >100 | 0.024 | Histone H2A; chromatin structure; ubiquitous; X16495 |
| 4 | 3 | 0.030 | Histone H2B; chromatin structure; ubiquitous; ET62908 |
| 7 | 8 | 0.006 | Histone H3; 1-D (H3-D) and histone H4-D (H4-D); chromatin structure; ubiquitous; U62672. |
| >100 | >100 | <0.001 | Histone H3.2-F (H3-F), histone H2a.1-F (H2a-F), histone H2b-F (H2b-F); chromatin structure; ubiquitous; U62669 |

TABLE 4-continued

| LTCR* | STCR* | P | GENE |
|---|---|---|---|
| | | | Liver specific and ubiquitous genes |
| 4 | 4 | 0.034 | HpaH tiny fragments locus 9c (Htf9c); structural similarity with yeast mucleic acid-modifying enzymes; activated at the G1/S transition, and S phase; down-regulated in growth arrested cells; liver (ubiquitous); X56044 |

*Fold of control

Example 18

CR Stimulates the Expression of Genes Enhancing Genetic Stability and Apoptosis The accumulation of genetic damage has been postulated to be a cause of aging. Without being limited to any specific mechanism, CR has been postulated to either reduce the rate of accumulation of genetic damage, or to enhance its rate of repair. Both long and short term CR enhanced the expression of numerous genes associated with DNA repair (Table 5). These genes included Xpa, which is involved in nucleotide excision DNA repair; and the Brca2 gene, which is important in DNA double-strand break repair and DNA damage-induced cell-cycle checkpoint activation.

A theory of aging closely related to the DNA damage theory proposes that the reduction of apoptosis with age, and its restoration with CR plays and important role in aging. This hypothesis purposes that the accumulation of damaged cells with age contributes to aging itself and to the onset of the diseases of aging. Long and short term CR greatly enhanced the expression of a number of genes which choreograph the progression of a cell through the apoptotic pathway (Table 5). These genes included Casp1, Casp3, Bax, and Bcl2 which code for key components of the apoptotic pathway.

TABLE 5

| LTCR* | STCR* | P | GENE |
|---|---|---|---|
| | | | Genetic stability and apoptosis |
| | | | DNA Replication/Repair |
| 9 | 8 | <0.001 | Antigenic determinant of rec-A protein (Kia); Kia17; DNA-binding nuclear protein upregulated in response to UV and ionizing radiation; accomulated in the nucleus of proliferating cells; ubiquitious; X58472 |
| >100 | >100 | 0.001 | Breast cancer 2 (brc32); DNA double-strand break repair and DNA damage-induced cell-cycle checkpoint activation; ubiquitous; ET62746 |
| 3 | 3 | 0.029 | DNA primase p49 subunit (Prim); DNA replication; liver (ubiquitdus); X74351 |
| 6 | 5 | 0.009 | Mut L. homologue 1 (*E. Coli*(M1h1); treanscription-coupled nucleotide excision repair; cell cycle checkpoint control; ubiquitous; ET63479 |
| 3 | 3 | 0.025 | Xeroderina pigmentosum complementation group A (Xpa); nucleotide excisine DNA repair; ubiquitous; X7435 |
| | | | Apoptosis |
| >100 | >100 | 0.001 | B-cell leukemia/lymphoma 2 (Bcl2); suppresses apoptosis by controlling mitochondrial membrane permeability; many cells and tissues; L31532 |
| >100 | >100 | <0.001 | Bcl2-associated X protein (Bax); pro-apoptotic activity; can form channels in lipid membranes; many cells and tissues; L22472 |
| 5 | 4 | 0.033 | Caspase 1 (casp1); cysteiac protease mediator of apoptosis; ubiquitous; U04269 |
| 2 | 3 | 0.000 | Caspase 3 (Casp3); cysteine protease mediator of apoptosis; ubiquitous; ET63241 |
| 3 | 4 | 0.005 | Cyclin G (Ccng); augments apoptosis; target gene of P53; liver, elsewhere; Z37110 |
| >100 | >100 | <0.001 | Fused toca (Fta); a gene related to ubiquitin-conjugating enzymes; suggested role in apoptosis during development; expression distribution poorly defined; X71978 |
| 22 | 21 | <0.001 | P53 specific ubiquitin ligase 2 (Mdm2); promotes ubiquitination and proteaesome degradation of p53; inactivation by stress causes cell cycle arrest and apoptosis; liver, elsewhere; X58876 |
| >100 | >100 | <0.001 | RNA-dependent EIF-2 alpha kinase; double-stranded RNA-dependent protein kinase; key mediator of antiviral effects of interferon; ubiquitous; ET61211 |
| >100 | >100 | 0.009 | Tumor necrosis factor (Tnf); Proapoptotic factor in liver; X02611 |

*Fold of control

Example 19

CR Activation of Genes of the Enteric Nervous System

The liver is a highly innervated organ. This innervation includes elements of the enteric nervous system, as well as sympathetic innervation in the small arteries of the hepatic mesentery. This nervous innervation is essential to the activity of the liver. Nervous innervation has a role in the release of glucose by hepatocytes in response to insulin. As shown in Table 6, long and short term CR activated the expression of a large number of genes associated with the membrane receptor signaling, including membrane receptors for protein and small molecule neurotransmitters, and for cell growth and maintenance factors. CR induced the expression of genes for both phosphatases and kinases involved in signaling by these receptors. CR also induced the expression of four neuronal tissue specific transcription factors (Table 6).

CR enhanced the ability of liver neurons to transduce and respond to nervous system signaling. Eight genes for membrane channels were induced, including genes for sodium, potassium, and water channels (Table 6). Also induced were a number of integral membrane proteins such as proteolipid protein and cadherin 8, as well as the products of 5 genes for molecular motors which are probably involved in neural plasticity and remodeling. These proteins included 4 members of the dynein, axon, heavy chain family. Our results are consistent with the idea that CR increases the remodeling and activity of hepatic nerves after only 4 weeks.

TABLE 6

| | | | Neuromal Cell Specific Genes |
|---|---|---|---|
| LTCR* | STCR* | P | GENE |
| | | | Signal Transduction |
| 19 | 18 | 0.001 | 5-hydroxytryptamine (serotonin) receptor 1E beta (Htrieb); G-protein-coupled receptor; CNS; Z14224 |
| >100 | >100 | <0.001 | Activia A receptor, type 1B (Acvt1b); limb development; embryo brain, dorsal rool ganglin, spinal cord, vibrisae, elsewhere; Z31663 |
| 5 | 5 | 0.005 | Ankynin 3 (Ank3); implicated in Na(+) channel clustering and activity; neurosal axons, wide distribution; ET62740 |
| 3 | 3 | 0.022 | Bone morphogenetic protein receptor, type 1B (Bmpr1b); activin receptor-like kinase-6; serine-threonine kinase; CNS, muscle, blood vessels, others; Z23143 |
| 5 | 6 | 0.004 | Discs, large homologue 1 (*Drosophila*) (Digh1); role in localization and function of glutamate receptors and K(+) channels; neurons, epithelial cells; ET61665 |
| 67 | 70 | 0.001 | Eph receptor A7 (Epo7); developmental kinase 1; member of receptor tyrosine kinase family; brain, testes and spleen; X79082 |
| >100 | >100 | 0.001 | Fibroblast growth factor 9 (Fgf9); autocrine/paracrine growth factor; embryonic acural cell differentiation; adult and developing acuronal cells, epithelial cells, others; U33535 |
| 14 | 15 | <0.001 | Fibroblast growth factor homologous factor 1 (Fgf1); nervous system development and function; highest in brain and skeletal muscle; U66201 |
| 17 | 19 | 0.003 | G-protein-coupled receptor, family C, group 1, member H (Gprc1b); glutamate receptor, metabotropic 8, CNS, glial cells, retina, olfactory bulb, stellate/basket cells; U17152 |
| 28 | 29 | <0.001 | Gamma-aminobutyric acid (GABA-A) receptor, subunit beta 3 (Gabrb3); links binding of GABA to inhibitory chloride flux; CNS; U14420 |
| 12 | 11 | <0.001 | Glutamic receptor, iosotropic, kainate 1 (Grik1); CNS; X66118 |
| >100 | >100 | 0.007 | Gosadotropia releasing hormone recepotr (Garbr); G-protein-coupled receptor; activates MAPK cascases; brain, anterior pituitary, reproductive organs; L28756 |
| 4 | 3 | 0.018 | H6 homeo box 2 (hmx2); specification of neuronal cells; developing CNS; S80989 |
| >100 | >100 | 0.001 | Histamine receptor H1 (Hrb1); coupled to phosphoisositide turnover-calcium mobilization signaling; regulates IGF-I expression, cell proliferation, several function; neurons, liver, elsewhere; D50095 |
| 64 | 73 | <0.001 | Neuropeptide Y receptor Y6 (Npy6r); regulates energy balance through its oranigenic, antithermogenic, and insulin secretagogue actions, neurons, vascular smooth muscle cells; U58367 |
| >100 | >100 | <0.001 | Paired-Ig-like receptor A1 (Pira1); activating receptor on B lymphocytes, deadritic and myeloid-linage cells; ET62839 |
| 4 | 4 | 0.003 | Preproglucagon (Ocg); glucagon-like peptides I and II; neuropeptide; CNS, pancreatic alpha cells, ileum, Z46845 |
| >100 | >100 | 0.013 | Protein kinase, cGMP-dependent, type II (Prkg2); signal transductions; brain, kidney, small intestine, colon; L12460 |
| >100 | >100 | 0.001 | Protein tyrosine phosphatase, receptor type, M (Ptprm); expressed in capillaries in developing neural tissue, lung; X58287 |
| >100 | >100 | <0.001 | Reluxin precursor (Rln); insulin gene family; remodeling of collagen; brain, uterus, prostate, pancrease and kidney; Z27088 |
| >100 | >100 | <0.001 | Ryanodine receptor 3 (Ryr3); intracellular Ca2+ channels; neurons, skeletal and smooth muscle; ET61090 |

TABLE 6-continued

| LTCR* | STCR* | P | GENE |
|---|---|---|---|
| | | | Neuroma1 Cell Specific Genes |
| | | | Neuronal Tissue Specific Transcription Factors |
| >100 | >100 | <0.001 | Atonal homologue 5 (*Drosophila*) (Aloh 5); neurogeain 3; transcription factor; neuroD-related bHLH protein; CNS; U76208 |
| 19 | 18 | 0.003 | Embigin (Emb); DNA-binding transcription factor; class Vt POU domain; CNS; D13801 |
| >100 | >100 | 0.026 | Paired box gene 6 (Pax6); transcription factor; development of CNS, eye; X63963 |
| >100 | >100 | <0.001 | Zinc finger protein 2 (Zfp2); Mkr-2; differentiation and/or maintenance of neurons; central and peripheral neurons; Y00850 |
| | | | Channels |
| 4 | 3 | 0.007 | Aquaporia 4 (Aqp4); allows water and small solutes through plasma membrane; brain and other tissues; U48397 |
| 5 | 6 | 0.004 | Discs, large homologue 1 (*Drosophila*) (Dlgh1); localization and function of glutamate receptors and K(+) channels; neural sysapacs; ET61665 |
| 22 | 25 | 0.001 | Gap junction membrane channel protein beta 6 (Gjb6); connexin 30; forms transmembranous gap junction channels between adjacent cells; brain, skin; ET63385 |
| 11 | 11 | 0.001 | K+ channel beta-subunit; ion channel; brain and kidney; X97281 |
| 14 | 16 | 0.001 | Potassium inwardly-rectifying channel, subfamily J, member 6 (Kcnj6); neurons; ET61642 |
| 8 | 8 | 0.005 | Potassium, voltage gated channel, shaker related subfamily, member 2 (Kena2); T cells, myelinating Schwann cells; M30440 |
| 27 | 28 | <0.001 | Sodium channel 27; brain; L22340 |
| 11 | 11 | <0.001 | Sodium channel, type X, alpha polypeptide (Scn10a); brain unmyelinated axons; Y09108 |
| | | | Molecular Motors |
| 2 | 2 | 0.004 | Dilute lethal-20J; Class-V myosin; vesicular membrane trafficking; transport of endoplasmic reticulum vesicles in neurons; M33467 |
| 7 | 8 | 0.001 | Dynein, axon, heavy chain 1 (Dashe1)k dyneins are molecular motors that drive the beating of cilis and flagella; brain, trachea, testis; ET63395 |
| >100 | >100 | <0.001 | Dynein, axon, heavy chain 3 (Dnahc3); brain, trachea, testis; ET63399 |
| 5 | 6 | 0.013 | Dynein, axon, heavy chain 6 (Dnahc6); brain, trachea, testis; ET63402 |
| 4 | 5 | 0.002 | Dynein, axon, heavy chain 9 (Dnahc9); brain, trachea, testis; ET63405 |
| | | | Cell Surface and Secreted Proteins |
| >100 | >100 | 0.001 | Cadherin 9 (Cdh8); adhesion molecule; subdivisions of the early CNS and thymus; ET63017 |
| 37 | 36 | <0.001 | Glutamic acid decarboxylase, 67 kD; responsible for gamma-aminobutyric acid synthesis; brain, islets; Y12257 |
| 2 | 2 | 0.011 | Glypius 4 (Gpc4); cell surface heparis sulfate proteoglycan; role in regulation of neural cell transition from proliferation to differentiation; neurons; X83577 |
| 19 | 20 | <0.001 | Neurexophilin 2 (Nxph2); neuronal glycoprotein; binds to alpha-neurexine; brain; U56650 |
| 13 | 13 | <0.001 | Neurotrophin 3 (Ntf3); secreted protein; resistenance and plasticity of neurons; enteric neurons, others; X53257 |
| 43 | 41 | 0.001 | Proteolipid protein (Plp), main integral protein of myelin; CNS; X07215 |
| 4 | 4 | 0.043 | Sema domain, immunglobulin domain (lg), short basic domain, secreted, (serinaphonin) 3E (Sema3e); glycoprotein involved in embryonic development; developing neural tubes, lungs, skeletal elements; ET63410 |
| >100 | >100 | <0.001 | Sema domain, seven thrombospondin repeats (type 1 and type 1-like) (Sema5a); axonal guidance; early embryogenesis; X97817 |
| | | | Other Genes |
| 6 | 7 | 0.015 | Disabled homolog 1 (*Drosophila*) (Dah1); adaptor molecule in neural development; neuronal and hematopoietic cells; ET63156 |
| 23 | 24 | <0.001 | Galanin (Gal); neuropeptide; enhances hepatic glucose production: hepatic nerves and elsewhere; L38580 |
| 3 | 4 | 0.006 | Netrin 1 (Nta1); axon outgrowth-promoting protein; guidance molecule; guides growing axons in development; CNS; U65418 |
| 127 | 129 | <0.001 | Nucleosome assembly protein 1-like 2 (Nap12); Bpx; brain; X92352 |
| >100 | >100 | <0.001 | Proteasecome 3 (Ptne3); Ki antigen; cell proliferation; enhances generation of class I binding peptides; liver, neurons, elsewhere; U60330 |

TABLE 6-continued

| Neuromal Cell Specific Genes | | | |
|---|---|---|---|
| LTCR* | STCR* | P | GENE |
| 58 | 58 | <0.001 | UDP-glucoronosyltransferase 8 (Ugt8); cerebroside and sulfatide biosynthesis; CNS and peripheral nervous system; X92122 |

*Fold of control

Example 20

Induction of Other Liver Specific Genes by CR

Of the approximately 200 genes reported to be expressed either liver specifically or ubiquitously, 13 code for cytokines or growth factors; 12 for cell surface receptors; 21 for signal transduction, cell cycle or cell growth related proteins; 4 for nuclear receptors, 20 for transcription factors; 6 for translation, splicing, or RNA processing related factors; and 9 for chromatin structure related genes (Table 4). The overall pattern of genes induced in this group of genes suggests that CR stimulates the growth, remodeling and responsiveness of liver cells to signaling systems. These results are consistent with those found for neuronal genes, discussed above.

Both long and short term CR induced the expression of the cell growth factors Tgfb2, Fgf1, Fgf2, Fgf3, Fgf7, Fgf9, Figf, Inhbb, Inhbe, and 3 interferon-related genes. Likewise, a large number of genes coding for cell cycle regulation were induced by CR. These genes included Ptpn16, Nck1, Plcg1, Map3k1, Mapk1, Madb5, Wnt10b , Ab1, and others. Without being limited to any specific mechanism, the hypothesis that CR induces cell remodeling and growth of liver cells is further supported by the observation that both long and short term CR very strongly induced the expression of 7 histone genes. In 6 cases, these mRNA levels were induced from undetectable, or nearly undetectable levels. Two other genes which appear to be associated with chromatin structural modification were also strongly induced by CR (Htf9c and homologous to Drosphila Hp1; Table 4). Further evidence that CR enhance cell division and remodeling is the up regulation of the mRNA for the transferrin receptor, which mediates cellular iron uptake, a process essential for cell growth and division.

Three receptor mRNAs associated with energy balance were induced by CR. Two of these were for neuropeptide Y receptor Y6 (Table 6) and pancreatic polypeptide receptor 1, and one was for the leptin receptor (Table 4).

Example 21

Global Hepatic Gene Expression Profile

We have tested the hypotheses that CR produces similar effects on gene expression early and late in life by examining the effects of aging and caloric intake on the expression of approximately 12,000 genes and ESTs in the liver of old (27-month-old) and young (7-month-old), control and CR mice, using [GeneChip] *oligonucleotide based high-density* microarrays. We found that CR produced a massive reprogramming of gene expression early and late in life. The patterns of expression induced by CR in young and old mice were highly homologous. Comparison of gene expression in the groups of mice indicated that CR only prevented age-related changes in the expression of a few genes. Examination of the genes involved does not support the idea that they have a principle role in the age-retarding effects of CR. Together, the results do not support the idea that CR acts principally to prevent deleterious age-related changes in gene expression. Instead, CR induces a highly-homologous, major reprogramming of gene expression in animals of all ages.

The average global hepatic gene expression profile for each group of mice, displayed using GeneSpring 3.0 (Silicon Genetics, San Carlos, Calif), is shown in FIG. 8. The GeneSpring experiment tree algorithm clustered gene expression in the young and old CR mice together, and separately clustered expression in the young and old control mice together. These results indicate that that the effects of the CR diet on gene expression was significantly greater than the effect of age. Further, these data indicate that CR produced homologous effects on gene expression in the young and old mice.

TABLE 7

Pairwise comparisons of the global gene expression correlation coefficients for each possible pair of mice.

| | Old-CR | Old-Control | Young-CR | Young-Control |
|---|---|---|---|---|
| Old-CR | 0.53 ± 0.02* | −0.09 ± 0.02 | 0.41 ± 0.04 | −0.10 ± 0.03 |
| Old-Control | | 0.28 ± 0.06 | −0.11 ± 0.03 | 0.23 ± 0.02 |
| Young-CR | | | 0.41 ± 0.01 | −0.06 ± 0.02 |
| Young-Control | | | | 0.22 ± 0.02 |

*All values average values, ± SD are calculated as the Log (1+ the mRNA level)

These conclusions are supported by comparison of the correlation coefficients calculated from the expression data for each possible pair of mice in the study (Table 7). Because the mice were genetically identical, infra-group values provide a measure of the maximum correlations attainable. Inter-group values measure the similarity between groups. Inter-group comparisons between young and old CR and control mice indicated that gene expression in all CR mice was highly homologous, regardless of the age of the animals. Likewise, regardless of age, the intra-group expression patterns of the control mice were highly homologous. In contrast, there was no intra-group correlation between mice in different dietary groups, regardless of age. These data indicate that the number of calories consumed, but not age was the major influence in determining the global patterns of gene expression in these mice. This novel result is fuirther supported by the analysis described below.

The patterns of gene expression in the mice were further evaluated by successive application of the Venn Diagram Function of GeneSpring 3.0, one-way ANOVA, and Fisher's test ($P<0.05$) to the levels of expression of each gene and expressed sequence tag (EST) in the 4 groups of mice. These operations sorted the genes and ESTs into one of 9 possible categories (Tables 8A and B). Only statistically significant differences of 2-fold or more are shown. The expression of most genes and ESTs were not affected by either CR (–80% unchanged) or aging (95% unchanged). Of the genes and ESTs which did changed expression among the groups, 5-times as many genes and ESTs changed expression level in response to CR (2456) as changed in response to age (561). Of the genes and ESTs responsive to CR, most (40%) were upregulated in both young and old mice. Two other groups of genes and ESTs were upregulated either in old mice only (28% of the genes that changed expression), or in young mice only (19% of the genes that changed expression). An even smaller number of genes and ESTs were down regulated by the CR diet in young or old mice (13% of the genes that changed expression).

TABLE 8

The effects of age and diet on gene expression a. Diet Effect

| Young | Old (CR/Control)* | | | |
|---|---|---|---|---|
| (CR/Control)* | Up** | Unchanged | Down** | Total |
| Up** | 975 (8.1%**) | 473 (3.9%) | 0 | 1448 |
| Unchanged | 685 (5.7%) | 9587 (79.6%) | 172 (1.4%) | |
| Down** | 0 | 105 (0.9%) | 46 (0.4%) | 151 |
| Total | 1660 | | 218 | |

b. Age Effect

| Control | CR (Old/Young)* | | | |
|---|---|---|---|---|
| (Old/Young)* | Up** | Unchanged | Down** | Total |
| Up** | 6 (0.05%***) | 136 (1.1%) | 2 (0%) | 144 |
| Unchanged | 186 (1.5%) | 11482 (95%) | 112 (0.9%) | |
| Down** | 1 (0%) | 113 (0.9%) | 6 (0.4%) | 119 |
| Total | 193 | | 119 | |

Example 22

208 Genes Greater in CR in Both Young and Old

Three novel conclusions can be drawn from these data. First, CR induced a substantial age-independent reprogramming of gene expression. A large number of genes and ESTs (975) were up regulated by CR in both young and old mice (Table 8A). In this group, 208 were known genes (See Appendix G) All of these known genes were among the group of 340 genes induced in 30 month old mice by both long-term CR (LT-CR; life-long) and short-term CR (ST-CR; only 4 weeks of CR). This highly reproducible, age-independent, responsiveness to CR suggests to us that these genes and ESTs are likely to mediate the life- and health-span extending effects of CR. At a minimum, the dietary responsiveness of these genes can be used as a gauge of the effectiveness of other treatments in reproducing the effects of CR on global patterns of gene expression. Further, because 90% of the genes and ESTs induced by lifelong CR (which includes the age-independent and age-dependent genes and ESTs) can be induced after only 4 weeks of CR, the vast majority of the genetic reprogramming induced by CR can be reproduced rapidly.

Example 23

142 Genes Up in Young CR But Not in Old CR

There is a second novel conclusion which can be drawn from the results in Table 8A . CR produced some "age-dependent" reprogramming of gene expression in both young and old mice. Of the 473 genes and ESTs induced by CR only in young mice, 142 are known genes (Appendix H) These results indicate that this subset of genes was also CR responsive in old mice, but not to sufficient levels that they were distinguished statistically from control expression levels in these studies. Thus, Table 8A overestimates the number of young-specific induced genes by approximately 25%. Of the young-specific genes, 8% are involved in transcriptional regulation; 5% are growth factors, cytokines or hormones; 18% are involved in signal transduction or cell cycle regulation; 14% are involved in embryogenesis and development; 14% are involved in cellular adhesion, or are components of the extracellular matrix or membrane; 7% are channels or ion pumps; 3% are involved in extracellular transport or secretion; 3% are involved in metabolism; 3% in DNA replication, repair or apoptosis; 3% in chromatin structure; 9% in immune function or in the primary response; and 15% are involved in other functions.

Example 24

200 Known Genes Greater in Old CR But Not in Young CR

Or the 685 genes and ESTs induced by CR in old mice, the identity of 200 are known (Table 8A); (Appendix I). Of these, 122 (61%) previously were shown to be induced by ST-CR in old mice. Thus, the majority are rapidly responsive to CR. Of the remaining 78 genes, approximately 12% are transcriptional regulators; 8% are growth factor, cytokines or hormones; 13% are involved in signal transduction or cell cycle regulation; 11% are involved in embryogenesis and development; 10% are involved in cellular adhesion, or are components of the extracellular matrix or membrane; 4% are channels or ion pumps; 4% are involved in extracellular transport or secretion; 3% are involved in metabolism; 3% in DNA replication, repair or apoptosis; 2% in chromatin structure; 3% in immune function or in the primary response; 2% in translation, splicing or RNA processing; 2% are cell surface receptors; and 23% are involved in other functions.

The proportion of genes involved in each functional category above are remarkably similar. Further, many of the genes induced by CR in young mice were members of similar gene families or were structurally or functionally related to genes induced only in old mice. These similarities suggest that CR has highly homologous age-specific effects. It is less likely that the relative proportion of genes falling into each category, and the identity of these genes is an artifact of the probes present on the chip. Firstly, all of the results are statistically significant. Second, the genomic profiles produced in several drug studies were strikingly different from those found here as to the identity of the genes affected, and their functional categories (data not shown). Together, these results indicate that CR has a robust, pervasive, and highly homologous effect in both young and old mice. It induced the expression of a substantial group of genes involved in a wide variety of cellular functions.

A commonly expressed view in the literature of CR and aging assumes tacitly or explicitly that CR acts by preventing deleterious, age-related changes in gene expression. This view is shown schematically in FIG. 9. This hypothesis assumes that prevention of age related changes in gene expression underlies the health- and life-span extending effects of CR. During aging, some genes become over expressed or under-expressed relative to their levels in young animals (lower and upper lines, FIG. 9). Some of these deviations are assumed to be deleterious. Preferably, no changes would change with time, and aging would either not occur or occur more slowly (center line, FIG. 9). In this view, CR should wholly or partially return over- or under-expressed genes to their youthful levels (arrows, FIG. 9). Although the reasoning is circular, some have said that if CR changes the expression of a gene toward the center line in the figure, it restored youthful levels of expression. We have analyzed the results of the studies reported here to evaluate this hypothesis further.

Of the approximately 12,000 genes and ESTs examined, aging of control mice increased the expression of 257 genes and ESTs, and decreased expression of 191 genes and ESTs (FIG. 9). Long-term CR wholly or partially, reversed or prevented 55 of the increases and 70 of the decreases. Short-term CR reversed 45 of the increases and 59 of the decreases in gene expression. Long-term and short-term CR both acted to reverse or prevent 23 of the increases and 41 of the decreases. Thus, long-term CR actually prevented the increased expression of only 32 genes and ESTs and the decreased expression of only 29 genes and ESTs. It is likely that the number of ESTs in each class overestimates the number of authentic genes in each category. First, the genes and ESTs which responded to CR in only 4 weeks are likely a subset of the genes and ESTs which respond acutely to CR. We have not yet examined longer times on the domain of genes responsive to acute CR. Some genes may be "slow changers" in response to acute CR. Second, we have found that many of the known genes present on these chips are redundant (e.g., multiple immunoglobulin genes of each class and T cell receptor genes, cloned chromosome break-points representing parts of two genes, uncharacterized chromosome regions, uninvestigated, unpublished cDNA sequences, etc.). For example, of the 23 genes and ESTs reduced to baseline expression levels only by LT-CR, 12 were known genes (Table 9). Of the 27 genes and ESTs which were decreased in expression by age and returned to baseline expression only by LT-CR, only 13 were from known genes (Table 10).

Of the 12 genes prevented from increasing with age by CR, few are involved in signal transduction. Rather, 6 are involved in immune system function, particularly in macrophage differentiation, proliferation, apoptosis, and activity. Of these, platelet-activating factor acetylhydrolase activity reduces plasma platelet activating factor mRNA levels. Platelet activating factor is a potent pro-inflammatory autacoid with diverse physiological and pathological actions. It does not seem likely that the return of these genes to baseline expression levels is due to a general reduction in inflammation, stress, or immune activity. In a previous study, we found that 61 immune system genes, including 6 primary response genes, and an additional 9 apoptotic genes were up regulated by both LT- and ST-CR in the liver of mice. Similar considerations apply to the other 6 genes in this group, and to the genes prevented from decreasing with age (Table 10). One can speculate about why reduction in the expression of the relatively few immune system specific, acute phase response genes and other genes listed in Table 9, or enhanced expression of the 13 immune system, and neuron or liver specific genes in Table 10 might be important in reducing the rate of aging. However, with few exceptions, very similar genes, and in some cases closely related family members of the genes in these lists are present in the group of 340 known genes induced by both LT- and ST-CR. Thus, it seems intuitively and statistically much more likely that the massive reprogramming of gene expression induced by CR (Tables 9 and 10) is responsible for the increase in life- and health-span induced by CR. The genes prevented from increasing and decreasing with age (Tables 9 and 10) seem much more likely to be the result, rather than the cause of these effects.

In summary, the studies presented here show that a major effect of CR is to massively (more than 10% of the genes and ESTs investigated) reprogram gene expression to a new pattern associated with slower aging and delayed onset of age-related diseases. This reprogramming includes age-independent induction of a relatively large group of genes and ESTs, as well as induction of smaller groups of genes age-dependently. Further, we found that age-related changes in gene expression are relatively rare. Even rarer are instances in which life-long CR prevents these changes. The rarity of such genes, and their identity suggest to as that they do not play a major role in the physiological effects of CR. The large and rapid response induced by CR on total liver gene expression suggests that major, systemic regulators of gene expression are altered by CR. Study of the regulation of a number of these genes should yield the identity of the regulators, and reveal how they are influenced by CR.

TABLE 9 mRNAs increased by age and returned to control levels by LT-CB

| GenBank | Phenotype |
|---|---|
| | Immune System |
| AF018268 | Apoptosis inhibitory 6 (Api6); a member of macrophage scavenger receptor cysteine-rich domain superfamily; inhibits apoptosis of a variety of cell types; secreted specifically by macrophages |
| M13018 | Cysteine rich intestinal protein (Crip); double zinc finger protein; expression changes with acute liver injury (cellular change); may function in cell proliferation, differentiation or turnover; high expression in immune cells, low in liver |
| J04596 | GRO1 oncogene (Gro1); encodes a cytokine; mediator of inflammatory and immune responses; also called melanoma growth-stimulatory activity; cell cycle regulator; platelets |
| L20315 | Macrophage expressed gene 1 (Mpeg1 or Mpg-1); increased when murine fetal liver hematopoietic progenitor cells induced to differentiate into macrophages; high levels in macrophages, moderate levels in certain myelomonocytic cell lines |
| U34277 | Phospholipase A2 group VII, platelet-activating factor acetylhydrolase, plasma (Pln2g7); secreted phopholipase A1 which modifies the pre-inflammatory platelet-activating factor (PAF) to yield the biologically inactive lyo-PAF; regulates baseline circulating PAF levels and may be critical in resolving inflammation; high PAF is a predictor of heart disease; liver macrophages |

TABLE 9-continued

| GenBank | Phenotype |
|---|---|
| | mRNAs increased by age and returned to control levels by LT-CB |
| L27990 | Sjogren syndrome antigen A1 (Seal); Ho52; stress response gene; ribonucleoprotein; macrophages |
| | Ubiquitous |
| D86729 | Heterogeneous nuclear ribonucleoprotein A1 (Hnrpa1); ribonucleoprotein, RNA processing; early down-regulation of this gene contributes to the cytotoxicity of the topoisomerase inhibitors that induce DNA cleavage; ubiquitous |
| U50850 | Retinoblastoma-like 2 (Rbl2); p130; transcriptional cell cycle repression through G1 phase (controls cyclia A, cdc 25G and cdc2 genes); tumor suppressor gene; expressed independently of retinoblastoma gene; expressed in embryo and ubiquitously in adult |
| U34042 | Tolloid-like (Tl1), an alternatively spliced product of the bone morphogenic protein-1 gene; metalloprotease purified from extracts capable of inducing ectopic bone formation; ubiquitous |
| | Liver Specific |
| U60438 | Serum amyloid A protein isoform 2 (Saa2); encodes an acute-phase reactant serum protein; liver |
| | Not Reported in Liver |
| M27501 | Protamine 2 (Prm2); compacting chromatin; expressed in posimiotic male germ cells during late stages of spermatogenesis |
| U52433 | Tubby (Tub); mutation is the tub gene causes maturity-onset obesity; adipocyte fat storage increased by 5–6 fold, insulin resistance; mutant mice have retinal and cochlear degeneration; gene function unknown; brain, hypothalamus, cochlea, retina |

TABLE 10

| GenBank | Phenotype |
|---|---|
| | mRNAs decreased by age and returned to control levels by LT-CB |
| | Immune System |
| M30903 | B lymphocyte kinase (Blk); sac-family protein tyrosine kinase; plays important role in B-cell development/activities and immune responses; B-lineage cells |
| U43384 | Cytochrome b-245, beta polypeptide (Cybb, cytochrome b558); integral component of the microbicidal oxidase electron transport chain of phagocytic cells, respiratory burst oxidase; phagocytes |
| U10871 | Mitogen activated protein kinase 14 (Mapk14); signal transduction, stimulate phosphorytation of transcription factors; major upstream activator of MAPKAP kinas 2; hematopoietic stem cells |
| Z22649 | Myeloproliferative leukemia virus oncogene (Mp1); Member of hematopoietic cytokine receptor family, cell cycle regulator, induces proliferation and differentiation of hematopoietic cell lines; hematopoietic precursor cells, platelets and megakaryocytes |
| Y07521 | Potassium voltage gated channel, Show-related subfamily member 1 (Kene1) potassium channels with properties of delayed rectifiers; nervous system, skeletal system, T lymphocytes |
| U87456 | Flavin-containing monooxygenase 1 (Fmo1); xenobiotic metabolism; highly expressed in liver, lung, kidney, lower expressed in heart, spleen, testis, brain |
| U40189 | Pancreatic polypeptide receptor 1 (Ppyr1), neuropeptide Y receptor, peptide Y receptor; G-protein-coupled receptor; liver, gastrointestinal tract, prostate, aeurosa endocrine cells |
| | Neuron Specific |
| U16297 | Cytochrome b-561 (Cyb561); electron transfer protein unique to aeuroendocrine secretory vesicles; vectoral transmembrane electron transport; brain |
| D50032 | Trans-golgi network protein 2 (Tiga2); integral membrane protein localized to the Trans-Golgi network; involved in the budding of exocytic transport vesicles; brain neurons |
| | Liver Specific/Ubiquitous |
| D82019 | Basigin (Bag), CD147, neurothelin; membrane glycoprotein, immunoglobulin superfamily, homology to MIICs, acts as an adhesion molecule or a receptor, neural network formation and tumor progression; embryo, liver and other organs |
| U38990 | Glucokinase (Gk), key glycolytic enzyme; liver |
| U50631 | Heat-responsive protein 12 (Hrp12); heat-responsive, phosphorylated protein sequence simularity to Hbp20; liver, kidney |
| U39818 | Tuberous sclerosis 2 (Tsc2); mutationally inactivated in some families with tuberous sclerosis; encodes a large, membrane-associated GTPase activating protein (GAP tuberlin); may have a key role in the regulation of cellular growth; ubiquitous |

Gene Expression in STZ-diabetic Mice

Streptozotocin (STZ) induces diabetes. Mice receiving three treatments with STZ were diabetic for about 4 weeks. Diabetes reduces insulin levels to almost zero. CR has a similar effect in that it lowers insulin levels, although not as low as in STZ-treated animals. Also, while CR lengthens life span, STZ has the opposite effect and shortens life span.

Figure 11:
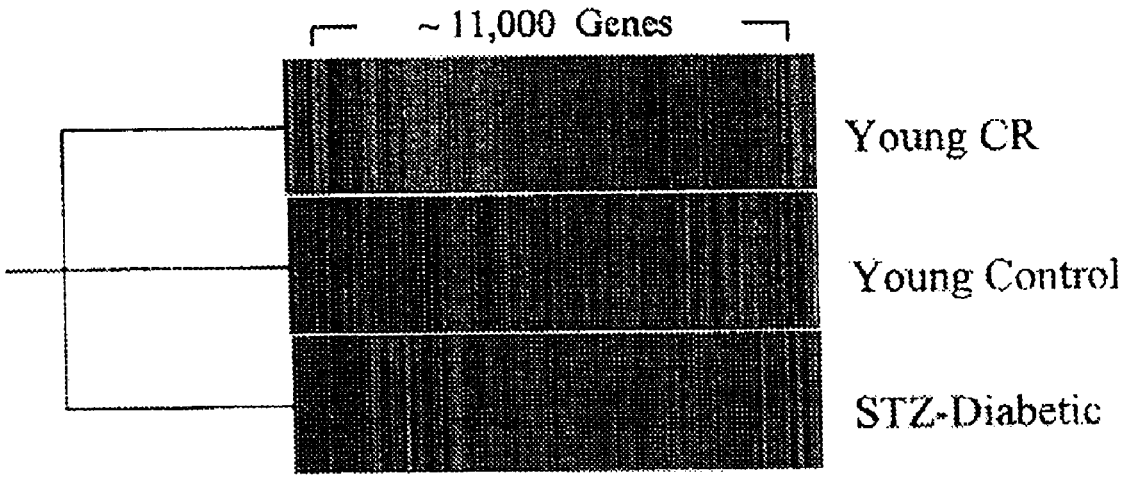

FIG. 10 shows pairwise comparison of global gene expression correlation coefficients for each possible mouse pair. The results indicate that hepatic gene expression is very different between young CR, young control and STZ-diabetic mice. FIG. 11 presents a visual profile which shows that the pattern of gene expression in the three groups is dissimilar. In conclusion, lowering insulin in the pathological way found in serious diabetes is insufficient to produce the gene expression profile or the life-span effects observed with CR.

Example 26

Gene Expression in Aminoguanidine Treated Mice

Aminoguanidine is believed to retard aging by preventing cross-linking of protein initiated by the aldehyde form of glucose. However, mice fed aminoguanidine exhibited little or no effect on life span. However, a large effect on gene expression was observed (FIG. 12). Gene expression for aminoguanidine-treated mice did not correlate with either old CR or old control. A visual representation of this finding is shown in FIG. 13. In conclusion, although aminoguanidine has little effect on aging in mice, major differences in gene expression are observed. These effects are not like those of CR, and this is consistent with the absence of a strong effect on the life-span of mice.

Example 27

To determine whether certain interventions mimic calorie restriction in mice, the following groups of mice are prepared.

Group 1: Controls

Group 2: Troglitazone (synthetic proposed calorie restriction mimetic drug that lowers insulin levels in rats and mice, lowers blood pressure and triglycerides, inhibits free radicals, increases mitochondrial mass, and doesn't seem to change food intake in rodents): treatment starts at 10 months Group 3: IGF-1 (natural proposed calorie restriction mimetic hormone that lowers both insulin and glucose levels and which may be directly involved in the basic mechanisms of aging; has rejuvenating effects on immune, muscular, and other systems): treatment starts at 12 months Group 4: ALT-711 (or other AGE breaking agent: proposed calorie restriction mimetic that acts by reversing the effects of elevated glucose levels as they occur or after they occur, rather than by reducing glucose levels): treatment starts at 18 months.

Animals in all groups will receive the same, known amount of food throughout the study.

Troglitazone and IGF-1 doses will be chosen to set glucose and insulin levels in the range for young or preferably calorie-restricted animals. Glucose and insulin will be measured but not controlled in the control and ALT-711 groups. Troglitazone will be supplied at a dose of ~0.2% of the diet (standard for troglitazone studies for other purposes). Similarly, ALT-711 will be incorporated into the diet. A low (two-toxic) level of ALT-711 is used that will remain constant over time.

It is assumed that IGF-1 will be supplied by injection (3 times per week, minimum) unless a continuous delivery method can be arranged. The preferred dosage method is implantation of non-dividing IGF-1-secreting cells, to attain steady IGF-1 levels, and if possible, this will be done. If this is not possible, IGF-1 will be obtained as a gift from Genentech or another manufacturer. Other possible alternatives to injection are: osmotic minipump; injection of IGF-1 into subcutaneous slow-release reservoirs; infusion by means of minipumps used by Celtrix; use of skin patches that allow slow-release to the body.

There will be 60 animals in each longevity-testing group (LTG). Each LTG will be accompanied by another set of, on average, 40 similarly-treated animals, which will be set aside for sacrifice to permit biochemical assays and histological documentation of the condition of the animals at fixed ages (sacrifice group, SG). In the case of the IGF-1 and troglitazone groups, some animals will be earmarked for pilot dose-finding experiments in a manner that will allow the average SG size to remain at 40, as described below. The groups earmarked for dose-verification will be referred to as the pilot dose groups, or PDGs.

For troglitazone, about a 2-month supply of each of three troglitazone diets (containing 0.1%, 0.2%, or 0.3% troglitazone) will be initially ordered. The main 0.2% troglitazone dose will be tested on a small pilot mouse population before committing the troglitazone group proper to this dose. If 0.2% troglitazone is not found to yield the expected changes in circulating insulin after 2 weeks on the 0.2% troglitazone, the diet will be changed to the more appropriate dose diet at that time and verified on a second small pilot mouse population.

Similarly, some animals will be used for IGP-1 injection pilot experiments to determine the proper starting dose.

At age 12 months: Sacrifice 3 animals/SG to obtain common baseline group of 12 animals to be compared to all subsequent results. This is the middle-aged universal control group. All subsequent data can be compared to the results for this pooled group.

At age 12.5 months: Begin the IGF-1 PDG with 7 mice given the best estimated dose of IGF-1. Sacrifice two weeks later for determination of insulin and glucose levels. Begin a verification/second trial dose of IGF-1 at 13 months, 1 week of ago, and sacrifice this second PDG at 13 months, 3 weeks of age. Assuming the assays for insulin and glucose can be completed in 1 week, this regimen will allow the final dose for the LTG to be determined prior to age 14 months. Similarly, at 12.5 months, place 7 mice on the 0.2% troglitazone diet. Two weeks later, sacrifice and assay for insulin and glucose. Begin adjusted-dose or verification dose group at 13 months, 1 week and sacrifice after two weeks.

At age 14 months: Begin troglitazone and IGF-1 at the experimentally-determined or estimated optimal doses for each.

At age 15 months: Sacrifice six animals from the IGF-1 and troglitazone SGs for determinations of glucose, insulin, and all other endpoints involved in the study. If necessary, adjust the IGF-1 dose again (both in the LTG and the untapped portion of the IGF-1 SG) and/or order diet with a modified troglitazone content. Sacrifice three animals each from the SGs for the controls and the ALT-11 groups and pool to create a common group of six animals for comparison to the IGF-1 and troglitazone groups.

At age 18 months: same as at 15 months, but use 7 mice/SG for IGF-1 and troglitazone and 4 mice/SG for the control and for the ALT-711 group. Begin the ALT-711 groups on ALT-711 immediately after this sampling.

At around 27 months (~24–30 months): Sample all remaining surviving SG mice.

If the total initial numbers of mice in the sacrifice groups for treatments 1, 2, 3, and 4 are 30, 50, 50, and 30, respectively, then if there were no mortality in any of these groups, there would be 20 animals left in each SG at the time of final sampling. But if we assume that only ⅓ of this number will be alive, then about 7 animals will remain to be sampled at the final sample time, or about the minimum required for statistical significance. It the mean survival rate at 27 month is over 73%, the 27 month end point may be postponed to a greater age.

In addition to other biochemical markers, assays may include:

heart and thymus volume and histology;

autoantibody titer,

T and B cell characteristics;

protein or albumin concentration in bladder urine at sacrifice;

molecular glycation indices;

protein carbonyl content or other free radical/oxidation indices; and incidence of neoplasia, esp. of prostate and breast.

What is claimed is:

[1. A method of identifiing an intervention that mimics the effects of caloric restriction in cells, comprising:

obtaining a biological sample;

exposing said biological sample to an intervention;

waiting a specified period of time;

assessing changes in gene expression levels, levels of RNA, protein, or protein activity levels related to one or more biomarkers of aging; and identifying said intervention as one that mimics the effects of caloric restriction if one or more changes in said levels also occurs in caloric restriction.]

[2. The method of claim 1 , wherein said biological sample comprises cells.]

[3. The method of claim 2, wherein said cells are obtained from a mammal.]

[4. The method of claim 3, wherein said mammal is a mouse.]

[5. The method of claim 1, wherein said change in gene expression levels, levels of RNA, protein, or protein activity levels corresponds to a change in gene expression for a gene encoding a chaperone protein.]

[6. The method of claim 5, wherein said gene encoding a chaperone protein is GRP78.]

[7. The method of claim 1, wherein said biomarker is apoptosis.]

[8. The method of claim 1, wherein said biomarker is aging.]

[9. The method of claim 8, wherein said biomarker of aging is a production of cancer cells.]

[10. The method of claim 1, wherein said changes in said gene expression level, levels of RNA, protein, or protein activity levels related to one or more biomarkers of aging occur in 6 weeks or less.]

[11. The method of claim 10, wherein said changes in said gene expression levels, levels of RNA, protein, or protein activity levels related to one or more biomarkers of aging occur is four weeks or less.]

[12. The method of claim 11, wherein said changes in said gene expression levels, levels of RNA, protein, or protein activity levels related to one or more biomarkers of aging occur in two weeks or less.]

[13. The method of claim 12, wherein said changes in said gene expression levels, levels of RNA, protein, or protein activity levels related to one or more biomarkers of aging occur in about two days or less.]

[14. A method according to claim 1 wherein changes in gene expression are evaluated using a gene chip.]

[15. The method of claim 14, wherein the gene chip contains genes for immune system activation.]

[16. The method of claim 14, wherein the gene chip contains genes for DNA repair.]

[17. The method of claim 14, wherein the gene chip contains genes associated with apoptosis.]

[18. The method of claim 14, wherein the gene chip contains genes for the enteric nervous system.]

[19. The method of claim 1, wherein said biological sample is a test animal.]

[20. The method of claim 19 additionally comprising determining changes in said levels in a reference animal having identifying characteristics of a long-term calorie-restricted animal wherein the reference animal has been on a calorie restricted diet for less than about 6 weeks and wherein said changes are used in said identifying said intervention as one that mimics the effects of calorie restriction.]

[21. The method of claim 20, wherein the reference animal has been on a calorie restricted diet for less than about 4 weeks.]

[22. The method of claim 20, wherein the reference animal has been on a calorie restricted diet for less than about 2 weeks.]

[23. The method of claim 19, wherein said test animal is a mouse.]

[24. The method of claim 19, wherein changes in gene expression are assessed in said test animal.]

[25. The method of claim 19 which further comprises:

obtaining a gene expression profile from a calorie-restricted reference animal;

comparing changes in gene expression for the test animal to the gene expression profile of the calorie-restricted reference animal; and identifying said intervention as one that mimics the effects of calorie restriction if the gene expression profile of the test animal is statistically similar to the gene expression profile of the calorie restricted animal.]

[26. The method of claim 25, wherein the gene expression profile of the test animal is determined to be statistically similar to the gene expression of the calorie restricted animal by one-way ANOVA followed by Fisher's test ($P<0.05$).]

*27. A method of identifying an intervention that mimics the effects of caloric restriction in cells, comprising:*

*obtaining a biological sample;*

*exposing the biological sample to an intervention;*

*waiting a specified period of time;*

*assessing changes in gene expression levels, levels of RNA, protein, or protein activity levels related to one or more biomarkers of aging; and*

*identifying the intervention as one that mimics the effects of caloric restriction if one or more changes in the levels also occurs in a reference animal subjected to short term caloric restriction.*

*28. The method of claim 27, wherein the short term caloric restriction is about two to about six weeks.*

*29. The method of claim 27, wherein the short term caloric restriction is about four weeks.*

*30. The method of claim 27, wherein the changes are determined in a test animal.*

*31. The method of claim 30, wherein the test animal is a mouse.*

*32. The method of claim 27, wherein the specified period of time is six weeks or less.*

*33. The method of claim 27, wherein the specified period of time is four weeks or less.*

*34. The method of claim 27, wherein the specified period of time is two weeks or less.*

*35. The method of claim 27, wherein the specified period of time is two days or less.*

*36. The method of claim 27, wherein the biomarker of aging is a gene encoding a chaperone protein.*

*37. The method of claim 36, wherein the chaperone protein is GRP78.*

*38. The method of claim 27, wherein the changes in gene expression are evaluated using an oligonucleotide-based high density array.*

*39. The method of claim 38, wherein the biomarker of aging is a gene encoding a protein involved in immune system activation.*

*40. The method of claim 38, wherein the biomarker of aging is a gene encoding a protein involved in DNA repair.*

*41. The method of claim 38, wherein the biomarker of aging is a gene encoding a protein involved in apoptosis.*

*42. The method of claim 38, wherein the biomarker of aging is a gene encoding a protein involved in the enteric nervous system.*

* * * * *